United States Patent
Sorba et al.

(10) Patent No.: US 8,841,288 B2
(45) Date of Patent: Sep. 23, 2014

(54) QUINOLIN-4 (1H)-ONE DERIVATIVES AS INHIBITORS OF PHOSPHATIDYLINOSITOL 3-KINASES

(75) Inventors: Giovanni Sorba, San Giusto Canavese (IT); Gian Cesare Tron, Novara (IT); Ubaldina Galli, Castagneto Po (IT); Alberto Massarotti, Prato Sesia (IT); Emilio Hirsch, Turin (IT); Elisa Ciraolo, Turin (IT); Tracey Pirali, Novara (IT)

(73) Assignees: Universtà Degli Studi di Torino, Torino (IT); Università Degli Studi del Piemonte Orientale "Amedeo Avogadro", Vercelli (IT)

( * ) Notice: Subject to any disclaimer, the term of this patent is extended or adjusted under 35 U.S.C. 154(b) by 0 days.

(21) Appl. No.: 13/988,979

(22) PCT Filed: Nov. 28, 2011

(86) PCT No.: PCT/IB2011/055346
§ 371 (c)(1),
(2), (4) Date: May 22, 2013

(87) PCT Pub. No.: WO2012/073184
PCT Pub. Date: Jun. 7, 2012

(65) Prior Publication Data
US 2013/0245005 A1    Sep. 19, 2013

(30) Foreign Application Priority Data
Dec. 1, 2010   (IT) .............................. TO2010A0956

(51) Int. Cl.
| | | |
|---|---|---|
| *A61K 31/5377* | (2006.01) | |
| *C07D 413/14* | (2006.01) | |
| *C07D 403/04* | (2006.01) | |
| *C07D 403/14* | (2006.01) | |
| *C07D 405/14* | (2006.01) | |
| *A61K 31/4709* | (2006.01) | |

(52) U.S. Cl.
CPC ............ *C07D 413/14* (2013.01); *C07D 403/04* (2013.01); *C07D 403/14* (2013.01); *C07D 405/14* (2013.01); *A61K 31/5377* (2013.01); *A61K 31/4709* (2013.01)
USPC ................ 514/211.01; 514/231.5; 514/235.2; 544/112; 544/128; 540/544

(58) Field of Classification Search
CPC ............ A61K 31/4709; C07D 413/14; C07D 403/04; C07D 403/14; C07D 405/14
USPC .................. 544/128, 112; 514/235.2, 211.01, 514/231.5; 540/544
See application file for complete search history.

(56) References Cited

FOREIGN PATENT DOCUMENTS

| WO | WO 01/53266 | 7/2001 |
| WO | WO 2004/016607 | 2/2004 |

OTHER PUBLICATIONS

Science (1999), vol. 286, 531-537.*
Cancer and Metastasis Reviews (1998), 17(1), 91-106.*
International Search Report for PCT/IB2011/055346 mailed Jan. 25, 2012.
Written Opinion of the International Searching Authority mailed Jan. 25, 2012.
J. Hollick et al., "Pyranone, Thiopyranone, and Pyridone Inhibitors of Phosphatidylinositol 3-Kinase Related Kinases, Structure-Activity Relationships for DNA-Dependent Protein Kinase Inhibition, and Identification of the First Potent and Selective Inhibitor of the Ataxia Telangiectasia Mutated Kinase", Journal of Medicinal Chemistry, American Chemical Society, vol. 50, No. 8, Apr. 1, 2007, pp. 1958-1972.
O. Barbeau et al., Quinolinone and Pyridopyrimidinone Inhibitors of DNA-Dependent Protein Kinase, Organic & Biomolecular Chemistry, vol. 5, No. 16, Aug. 21, 2007, pp. 2670-2677.

* cited by examiner

*Primary Examiner* — Rebecca Anderson
(74) *Attorney, Agent, or Firm* — Nixon & Vanderhye P.C.

(57) ABSTRACT

Compounds of Formula (I): able to inhibit kinase activity, in particular Phosphatidylinositol 3-Kinases activity. The disclosure also relates to the use of compounds of Formula (I) for treatment of pathological conditions associated to alterations in Phosphatidylinositol 3-Kinases activity.

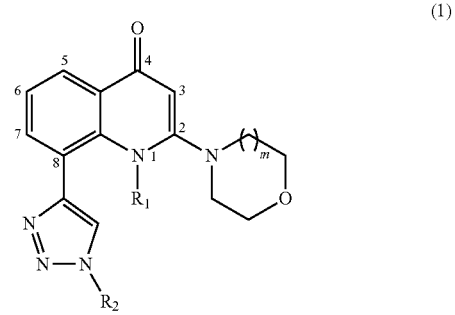

(1)

8 Claims, No Drawings

QUINOLIN-4 (1H)-ONE DERIVATIVES AS INHIBITORS OF PHOSPHATIDYLINOSITOL 3-KINASES

This application is the U.S. national phase of International Application No. PCT/IB2011/055346 filed 28 Nov. 2011 which designated the U.S. and claims priority to IT TO2010A000956 filed 1 Dec. 2010.

FIELD OF THE INVENTION

This disclosure concerns new compounds able to inhibit kinase activity, in particular the activity of the Phosphatidylinositol 3-Kinases.

The disclosure also relates to the use of these new compounds for treatment of pathological conditions associated to alterations in Phosphatidylinositol 3-Kinases activity.

BACKGROUND OF THE INVENTION

Class I Phosphatidylinositol 3-Kinases (PtdIns3Ks or PI3Ks) are heterodimeric lipid kinases consisting of a p110 catalytic subunit complexed to a regulatory subunit.

Class I of PI3Ks is composed of four isoforms which share a high degree of homology in the catalytic domain located towards their C-terminus. However, differences in the protein structure outside the catalytic domain and in the activation mechanisms allow to divide class I PI3Ks into class Ia and class Ib subclasses (Vanhaesebroeck et al. *Proc. Natl. Acad. Sci., U.S.A.*, 1997; 94:4330-4335).

Class Ia enzymes consist of three distinct catalytic subunits (p110α, p110β and p110δ) that dimerise with five distinct regulatory subunits (p85α, p55α, p50α, p85β and p55γ) and all catalytic subunits are able to interact with all regulatory subunits to form a variety of heterodymers.

The unique member of class Ib PI3K (PI3Kγ) consists of a p110γ catalytic subunit that interacts with p101 and p87 regulatory subunits.

Furthermore, while all class Ia PI3K (PI3Kα, β and δ) enzymes are activated by tyrosine kinase receptors (RTKs), class Ib enzyme is triggered uniquely by G protein coupled receptors (GPCRs, Katso et al. *Annu. Rev. Cell Dev. Biol.* 2001; 14:615-675).

These enzymes phosphorylate phosphatidylinositol on the D-3 position of the inositol head group.

Phosphorylated forms of phosphatidylinositol are called phosphoinositides.

Although all class I PI3Ks are able to produce in vitro Phosphatidylinositol (3,4,5)-trisphosphate (PtdIns(3,4,5)$P_3$), Phosphatidylinositol (3,4)-bisphosphate (PtdIns(3,4)$P_2$) and Phosphatidylinositol (3)-phosphate (PtdIns(3)P), in vivo they are responsible for the production of PtdIns(3,4,5)$P_3$ only.

The PtdIns(3,4,5)$P_3$ metabolism is finely tuned and results from the balance between production and degradation. While PI3Ks regulate PtdIns(3,4,5)$P_3$ production, the phosphatase PTEN degrades the PtdIns(3,4,5)$P_3$ to PtdIns(4,5)$P_2$ thus reducing the intracellular levels of the PtdIns(3,4,5)$P_3$ and turning off the signaling cascade initiated by PI3K.

PtdIns(3,4,5)$P_3$, generated by PI3Ks, acts as second messenger recruiting kinases with lipid binding domains (including plekstrin homology region, PH).

Major effectors of PI3Ks are the phosphoinositide-dependent kinase 1 (PDK1) and the serine-threonine protein kinase B/Akt which in turn mediates important biological effects of the PI3K pathway. Targets of Akt include transcription factors (e.g. FOXOs) and other kinases such as the mammalian target of rapamycin (mTOR) which regulates protein synthesis and cell growth.

Hence, when activated, class I PI3Ks, through PtdIns(3,4,5)$P_3$ production, contribute to signaling cascades that influence cell proliferation and survival, insulin signaling, mitogenic responses and cell motility.

Being involved in cell proliferation and survival, the PI3K signaling pathway was found frequently altered in human cancer. Such alterations may occur upstream and/or downstream PI3K or may influence its lipid kinase activity (Hirsch et al. *Pharmacol. Ther.* 2008; 118:192-205).

Since RTKs activate PI3K, their over-expression or hyper-activation (increased kinase activity), often occurring during tumorigenesis, enhances the PI3K signaling which in turn results in increased cell proliferation and survival. As an example, it has been shown that in breast cancer over-expression of the ErbB2 cause hyper-activation of the PI3K signaling pathway (Fry M J. *Breast Cancer Res.* 2001; 3:304-312; Engelman J A. *Nature Reviews Cancer* 2009; 9: 550-562; Hirsch et al. *Pharmacol. Ther.* 2008; 118:192-205).

Alterations downstream PI3Ks often affect the phosphatase PTEN. During tumor development, mutations and deletions of PTEN inactivate its phosphatase activity thus increasing intracellular levels of PtdIns(3,4,5)$P_3$ produced by PI3Ks. Genetic inactivation and loss of PTEN occurs frequently in many tumors such as glioblastoma, endometrial, prostate, lung and breast cancer (Bunney et al. *Nat. Rev. Cancer* 2010; 10: 342-352). Recent data have shown that, in a mouse model of prostate cancer, PTEN loss-driven tumorigenesis depends on PI3Kβ (Jia et al. *Nature* 2008; 454:776-779).

On the other hand, hyper-activating mutations and overexpression of PI3Ks cause increased PI3K lipid kinase activity with a consequent enhancement of PtdIns(3,4,5)$P_3$ production. In this context PI3Ks are able to activate the downstream pathways even in the absence of stimulation by growth factors.

Consistent with this view, the gene encoding for PI3Kα (PIK3CA) is frequently mutated in human tumors. Somatic mutations of the PIK3CA gene have been reported in several cancer types including colon, ovary, breast, brain, liver, stomach, endometrial and lung cancer (Samuels et al. *Science* 2004; 304:554). Three hot-spot mutations (E542K, E545K, and H1047R) represent 80% of all PIK3CA mutations found in tumors.

To date, no genetic alterations have been found in the genes encoding for PI3Kβ, PI3Kγ and PI3Kδ.

Conversely, increased expression of PI3Kβ and PI3Kδ occurs in glioblastomas (Knobbe et al. *Brain Pathol.* 2003; 13:507-518), colon and bladder tumors (Benistant et al. *Oncogene* 2000; 19:5083-5090). Moreover, overexpression of wild-type PI3Kβ, PI3Kδ and PI3Kγ is sufficient to induce an oncogenic phenotype in cultured cells (Kang et al. *Proc. Natl. Acad. Sci. USA* 2006; 103:1289-1294). These findings suggest that PI3Kβ, PI3Kγ and PI3Kδ exert their oncogenic potential as wild-type proteins.

Several somatic mutations have also been reported for the gene that encodes for the regulatory subunit of Class Ia PI3K, p85α. Analysis of the mutations has revealed that these mutants lose their inhibitory activity on the p110 catalytic subunit, thus causing deregulated activation of all isoforms PI3Kα, PI3Kβ and PI3Kδ (Jaiswal et al. *Cancer Cell* 2009; 16:463-474).

The essential role of PI3K in human cancer made of this pathway an attractive target for molecularly targeted anticancer therapy. In the last years, academia and industry multiplied their efforts for the development of several pan-specific or isoform-specific PI3K inhibitors.

In addition to the role of PI3K in proliferative and survival signaling in tumors, class Ia PI3K may also mediate angiogenic events in endothelial cells in response to pro-angiogenetic factors such as the vascular endothelial growth factor (VEGF, Jiang et al. *Adv Cancer Res.* 2009; 102:19-65).

On the other hand, experimental observations have demonstrated that PI3K, and in particular PI3Kγ and PI3Kδ, are important mediators in the signaling cascade leading to the initiation of the inflammatory response. Given their central role in inflammation, both PI3Kγ and PI3Kδ have recently been investigated as new potential therapeutic targets for diseases caused by dysfunctional immune responses which include autoimmune disorders, allergic disorders, respiratory diseases and all pathologic conditions whose onset and/or progression is driven by an inflammatory insult, such as myocardial infarction and atherosclerosis (Ghigo et al. *Bioessays* 2010; 32:185-96).

In the light of these evidences, class I PI3K inhibitors might be useful in preventing inflammatory cell recruitment in a range of inflammatory and autoimmune diseases.

Moreover, since PI3Kγ and PI3Kβ are implicated in platelet aggregation, these enzymes have emerged as new targets in the treatment of thromboembolism (Hirsch et al. *Thromb. Haemost.* 2006; 95:29-35; Canobbio et al. *Blood* 2009; 114: 2193-2196).

SUMMARY OF THE INVENTION

The object of this disclosure is to provide new compounds which exhibit biological activity against PI3K signaling pathway.

According to the invention, the above object is achieved thanks to the subject matter recalled specifically in the ensuing claims, which are understood as forming an integral part of this disclosure.

The present invention provides a class of 8-(1H-1,2,3-triazol-4-yl)quinolin-4(1H)-one compounds as a novel class of PI3K inhibitors and to their use in therapy.

More particularly, the invention provides a family of quinolin-4(1H)-ones with at 2-position a morpholine or an homomorpholine group and at 8-position a N-substituted 1,2,3-triazole.

The present disclosure provides a compound of formula (I):

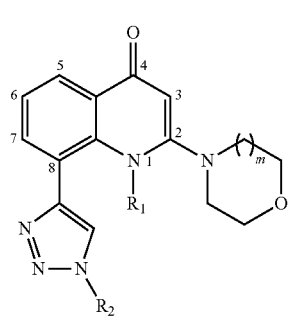

(1)

wherein
$R^1$ is H, straight or branched, substituted or unsubstituted $C_{1-8}$ alkyl,
$R^2$ is H, straight or branched, substituted or unsubstituted $C_{1-8}$ alkyl, substituted or unsubstituted $C_{3-6}$ cycloalkyl, $Ar^2$, $(CH_2)_n$—$C_{1-8}$ alkyl, or $(CH_2)_n$—$Ar^2$, wherein n is an integer 1 to 4, m is an integer 1 to 2,
$Ar^2$ is a substituted or unsubstituted aryl or heteroaryl group,
pharmaceutically acceptable tautomer, hydrate, solvate or salt thereof, or a pharmaceutically acceptable pro-drug thereof.

The disclosure relates to 8-(1H-1,2,3-triazol-4-yl)quinolin-4(1H)-one compounds of formula (I) with a specific PI3K enzymes inhibitory activity and a cytostatic and/or cytotoxic effect on tumor cells.

The disclosure also relates to the use of the 8-(1H-1,2,3-triazol-4-yl)quinolin-4(1H)-one compounds of formula (I) for in vivo treatment of pathological conditions associated with the over-expression and/or hyperactivation of PI3Ks, such as cancer, inflammation, ischemic diseases.

The disclosure also provides pharmaceutical compositions comprising at least one 8-(1H-1,2,3-triazol-4-yl)quinolin-4(1H)-one compound of formula (I) and a pharmaceutically acceptable carrier. The pharmaceutical composition may further comprise one or more additional therapeutic agents.

DETAILED DESCRIPTION OF THE INVENTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

An embodiment of the present disclosure provides compounds of formula (I):

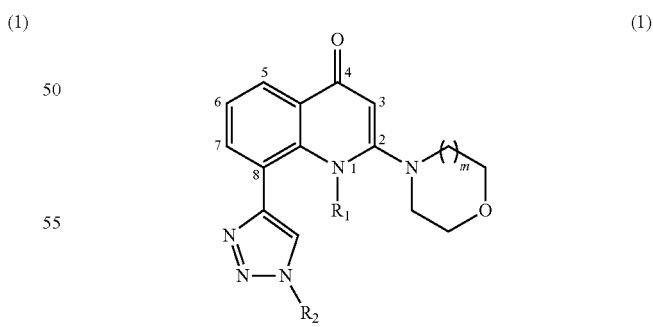

(1)

wherein
$R^1$ is H, or straight or branched, substituted or unsubstituted $C_{1-6}$ alkyl,
$R^2$ is H, straight or branched, substituted or unsubstituted $C_{1-6}$ alkyl, substituted or unsubstituted $C_{3-6}$ cycloalkyl, $Ar^2$, $(CH_2)_n$—$C_{1-8}$ alkyl, or $(CH_2)_n$—$Ar^2$, n being an integer 1 to 4, m is an integer 1 to 2,
$Ar^2$ is a substituted or unsubstituted aryl or heteroaryl group, pharmaceutically acceptable tautomers and/or hydrates and/or solvates and/or salts and/or pro-drugs thereof.

In an embodiment, when $R^1$ is a substituted $C_{1-6}$ alkyl, the one or more substituents are independently selected from halogen atoms, —$NH_2$, —$NHR^3$, —$NR^3R^4$, —OH, —$OR^2$, —$S(O)R^3$, —$S(O)_2R^3$, —$NHCOR^3$, —$NHSO_2R^3$, —$CONHR^3$, —$CONR^3R^4$, —$SO_2NHR^3$, —COOH, —$COOR^3$,
wherein
$R^3$ and $R^4$ are identical or different from each other and independently selected from —H, straight or branched, substituted or unsubstituted $C_{1-8}$ alkyl, substituted or unsubstituted $C_{3-6}$ cycloalkyl, $Ar^3$ and $Ar^4$ groups,
$Ar^3$ and $Ar^4$ are substituted or unsubstituted aryl or heteroaryl groups.

In an embodiment, when $R^2$ is selected from a substituted $C_{1-8}$ alkyl, $C_3-C_6$ cycloalkyl, $(CH_2)_n$—$C_{1-8}$ alkyl, the one or more substituents are independently selected from halogen atoms, tetrazole, —COOH, —OH, —$NH_2$, —$COOR^5$, —$NO_2$, —$CF_3$, —CN, —$OR^5$, —$CONH_2$, —$CONHR^5$, —$CONR^5R^6$, —$NHR^5$, —$NR^5R^6$, —$NHCOR^5$, —$NHSO_2R^5$, —$SO_2NHR^5$, —$SO_2NR^5R^6$, —$NHCONHR^5$, —$NHCONR^5R^6$, —$NHCOR^5$,
wherein
$R^5$ and $R^6$ are identical or different from each other and independently selected from —H, straight or branched, substituted or unsubstituted $C_{1-8}$ alkyl, substituted or unsubstituted $C_{3-6}$ cycloalkyl, $Ar^5$ and $Ar^6$ groups,
$Ar^5$ and $Ar^6$ are independently a substituted or unsubstituted aryl or heteroaryl group.

In an embodiment, when any of $R^3$, $R^4$, $R^5$, $R^6$, if present, are independently selected from a substituted $C_{1-8}$ alkyl and $C_{3-6}$ cycloalkyl, the one or more substituents are independently selected from halogen atoms, tetrazole, —COOH, —OH, —$NH_2$, —$COOR^7$, —$NO_2$, —$CF_3$, —CN, —$OR^7$, —$CONH_2$, —$CONHR^7$, —$CONR^7R^8$, —$NHR^7$, —$NR^7R^8$, —$NHCOR^7$, —$NHSO_2R^7$, —$SO_2NHR^7$, —$SO_2NR^7R^8$, —$NHCONHR^7$, —$NHCONR^7R^8$, —$NHCOR^7$,
wherein
$R^7$ and $R^8$ are identical or different from each other and independently selected from —H, straight or branched, substituted or unsubstituted $C_{1-8}$ alkyl, $C_{3-6}$ cycloalkyl, $Ar^7$ and $Ar^8$ groups,
$Ar^7$ and $Ar^8$ are independently a substituted or unsubstituted aryl or heteroaryl group.

In an embodiment, when any of $Ar^2$, $Ar^3$, $Ar^4$, $Ar^5$, $Ar^6$, $Ar^7$, $Ar^8$ groups, if present, are independently selected from a substituted aryl or heteroaryl group, the one or more substituents are independently selected from halogen atoms, tetrazole, —COOH, —OH, —$NH_2$, —$COOR^9$, —$NO_2$, —$CF_3$, —$OCF_3$, —CN, —$OR^9$, —$CONH_2$, —$CONHR^9$, —$CONR^9R^{10}$, —$NHR^9$, —$NHCOR^9$, —$NHSO_2R^9$, —$SO_2NHR^9$,
wherein
$R^9$ and $R^{10}$ are identical or different from each other and independently selected from —H, straight or branched, substituted or unsubstituted $C_{1-8}$ alkyl, substituted or unsubstituted $C_{3-6}$ cycloalkyl, $Ar^9$ and $Ar^{10}$ groups,
$Ar^9$ and $Ar^{10}$ are independently a substituted or unsubstituted aryl or heteroaryl group.

In an embodiment, any of $Ar^2$, $Ar^3$, $Ar^4$, $Ar^5$, $Ar^6$, $Ar^7$, $Ar^8$, $Ar^9$, $Ar^{10}$ groups, if present, are independently selected from benzene, furan, thiophene, pyrrolidine, pyrrole, pyrazole, imidazole, oxazole, isooxazole, triazole, isothiazole, 1,2,3-oxadiazole, 1,2,4-oxadiazole, 1,2,5-oxadiazole, pyridine, pyrididazine, pyrimidine, pyrazine, naphthalene, indole, isoindole, indolizine, benzofuran, benzothiophene, quinoline, isoquinoline, quinoxaline, carbazole, 1,2,3-triazole, 1H-indazole, 1H-benzo[d]imidazole, benzo[d]thiazol-2-amine.

The insertion of a N-substituted triazole at 8 position of the compounds of formula (I) originates novel interactions with the aminoacids belonging to the external part of the active site of the enzyme. Such novel compounds can lead to an increased activity or selectivity among the different class I PI3K enzymes. The triazole can act either as an active pharmacophore or as a simple linker which allows the perfect interaction between the inhibitor and the aminoacids of the active site of the enzyme.

Various 8-substituted-2-morpholin-4-ylquinolin-4(1H)-ones (disclosed in the international application WO-A-01/53266) have been used as inhibitors for specific kinases. However, none of the compounds disclosed in this publication corresponds to any compound of the present invention. Herein, the judicious use of specific 1,4-disubstituted triazole at the 8 position in the compounds of formula (I) allows, in specific cases, a significant improvement of potency against class PI3K enzymes, compared to the activity of the compounds described in the international application WO-A-01/53266.

Compounds of formula (I) herein described are useful for the treatment of disease condition depending on biological responses requiring signaling transduction events that require PI3K. In this condition, activation of PI3K leads to PIP3 production and activation of the downstream target.

Accordingly, the compounds of formula (I) are useful for the prevention or treatment of i) autoimmune diseases, preferably selected from lupus erythematosus, psoriasis, rheumatoid arthritis and ii) acute and/or chronic inflammation disorders, preferably selected from ulcerative colitis, asthma, chronic obstructive pulmonary disease (COPD), acute respiratory distress syndrome (ARDS), allergic rhinitis, anaphylaxis, cystic fibrosis, myocardial infarction, heart failure, ischemic diseases and atherosclerosis.

The compounds of formula (I) are also useful for the prevention or treatment of diseases that involve platelets aggregation, such as thrombosis.

The compounds of the formula (I) are useful for the treatment of tumor and cancer types that showed alteration of the PI3K pathway. The PI3K signaling pathway may be altered by: mutations of RTKs which cause strong activation of PI3K pathway even in the absence of growth factors; overexpression of RTKs with consequent higher recruitment and activation of PI3K to the plasma membrane; mutations of PI3Kα which lead to increase of its lipid kinase activity; overexpression of PI3Kα, PI3Kβ, PI3Kγ and PI3Kδ; mutations or deletions of PTEN which result in increased PtdIns(3,4,5)P$_3$ production.

Tumors and cancers where the PI3K pathway was found deregulated include i) solid tumors, preferably selected from breast, liver, ovary, cervix, prostate, testis, genitourinary tract, esophagus, larynx, thyroid, bone, colon, stomach, kidney, lung, non-small cell lung, skin and pancreas carcinomas as well as glioblastoma, neuroblastoma, keratoacanthoma, sarcoma, adenoma, seminoma and ii) hematological malignances preferably selected from Acute lymphoblastic leukemia (ALL), Acute myelogenous leukemia (AML), Chronic lymphocytic leukemia (CLL), Chronic myelogenous leukemia (CML), Acute monocytic leukemia (AMOL), Hodgkin's lymphomas (all four subtypes), Non-Hodgkin's lymphomas (all subtypes) and other leukemias.

Compounds of formula (I) can be administered in various routes appropriate to the condition to be treated.

Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. When the compound/s is/are administered orally, it/they may be formulated as pills, tables, capsules, ingested daily or less frequently for a specific period of time.

The dosage depends on a variety of factors including the age, weight and condition of the patient and the route of administration. Although daily dosage can vary from one individual to another, the compound/s will be administered to an adult human in a range of 0.0001-50 mg/kg of body weight as daily single dose or 0.01 to 1 mg/kg as daily repeated doses.

Compounds of formula (I) can be formulated as a pharmaceutical composition in the form of tablet, capsule, aqueous solution, granule, powder, suspension, cream, syrup, gel, emulsion, etc.

Tablets contain the compound/s of formula (I) in a mixture with non-toxic pharmaceutically excipients suitable for the manufacture of tablets. Exemplary excipients could be: inert diluents, such as sodium carbonated, lactose, dextrose, cellulose etc.; granulating and disintegrating agents as maize starch, blycolate, alginic acid; binding agents as gelatin or acacia; lubricating agents, for example silica magnesium or calcium stearate, stearic acid or talc.

For preparing suppositories, a mixture of for example fatty acid glycerides or cocoa butter is first melted and the compound/s of formula (I) is/are dissolved homogenously by stirring. The homogenous mixture is then cooled into convenient sized molds.

Liquid preparations, which include solutions, suspensions and emulsions, contain the formula (I) compound/s in a mixture of excipients suitable for the manufacture of aqueous suspension such as sodium carboxymethylcellulose, methylcellulose, resin, sodium alginate and natural or synthetic gums. Eventually the liquid preparation may contain suitable colorants, flavors, stabilizers, preservatives and thickening agents as desired.

Prodrugs of the compounds of formula (I) are also within the scope of the present disclosure. The term "prodrug" refers to a derivative that is converted into a compound of formula (I) by a reaction under physiological conditions with an enzyme, a gastric acid or in the living body through oxidation, reduction, hydrolysis or enzymatic reaction.

Examples of a prodrug are compounds, wherein an amino group in a compound of formula (I) is acylated to form, e.g., eicosanoylamino, alanylamino, pivaloyloxymethylamino or wherein the hydroxyl group is acylated, alkylated, phosphorylated e.g. acetyloxy, palmitoyloxy, pivaloyloxy, succinyloxy, fumaryloxy, alanyloxy or wherein the carboxyl group is esterified or amidated.

These prodrugs can also be produced from compounds of formula (I) according to well-known methods.

Metabolites of compounds of formula (I) are also within the scope of the present disclosure. The term "metabolites" refers to all molecules derived from any of the compounds in a mammal cell or organism.

Metabolite products typically are identified by preparing a radiolabeled ($^{14}C$ or $^{3}H$) isotope of a compound of the disclosure, administering it parenterally in a detectable dose, more than 0.5 mg/kg of body weight, to an animal such as rat, mouse, guinea pig, monkey, or to human, allowing a sufficient time for metabolism (max 30 hours) and isolating its conversion products from blood, urine or other biological samples. The metabolite structures are determined by MS, LC/MS or NMR analysis.

Preferred 8-(1H-1,2,3-triazol-4-yl)quinolin-4(1H)-one compounds of formula (I) are shown in Table 1.

TABLE 1

| Name | Structure |
|---|---|
| 8-(1-benzyl-1H-1,2,3-triazol-4-yl)-2-morpholinoquinolin-4(1H)-one | 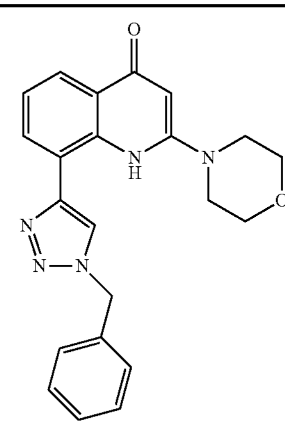 |
| 2-morpholino-8-(1-phenyl-1H-1,2,3-triazol-4-yl)quinolin-4(1H)-one | 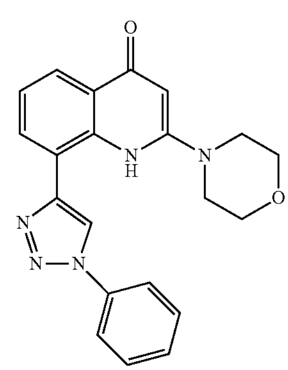 [SMILES: O=c1cc(N2CCOCC2)[nH]c2c(-c3cn(-c4ccccc4)nn3)cccc12] |

TABLE 1-continued

| Name | Structure |
|---|---|
| 2-(4-(4-(2-morpholino-4-oxo-1,4-dihydroquinolin-8-yl)-1H-1,2,3-triazol-1-yl)phenyl)acetonitrile | |
| 8-(1-(3-methoxyphenyl)-1H-1,2,3-triazol-4-yl)-2-morpholinoquinolin-4(1H)-one | 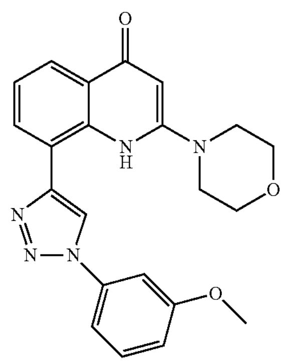 [SMILES: COc1cccc(-n2cc(-c3cccc4c(=O)cc(N5CCOCC5)[nH]c34)nn2)c1] |
| 2-morpholino-8-(1-(pyridin-4-yl)-1H-1,2,3-triazol-4-yl)quinolin-4(1H)-one | 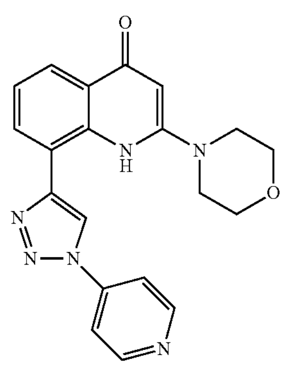 [SMILES: O=c1cc(N2CCOCC2)[nH]c2c(-c3cn(-c4ccncc4)nn3)cccc12] |
| 8-(1-(2-hydroxyphenyl)-1H-1,2,3-triazol-4-yl)-2-morpholinoquinolin-4(1H)-one | 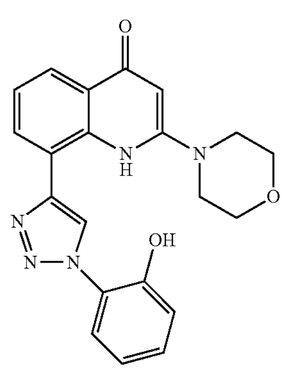 [SMILES: O=c1cc(N2CCOCC2)[nH]c2c(-c3cn(-c4ccccc4O)nn3)cccc12] |

TABLE 1-continued

| Name | Structure |
| --- | --- |
| 8-(1-(4-(benzyloxy)phenyl)-1H-1,2,3-triazol-4-yl)-2-morpholinoquinolin-4(1H)-one | 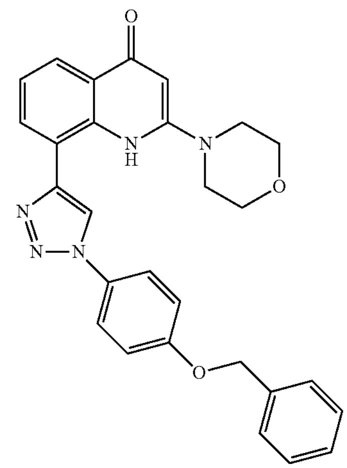 [SMILES: O=c1cc(N2CCOCC2)[nH]c2c(-c3cn(-c4ccc(OCc5ccccc5)cc4)nn3)cccc12] |
| methyl 4-((4-(2-morpholino-4-oxo-1,4-dihydroquinolin-8-yl)-1H-1,2,3-triazol-1-yl)methyl)benzoate | 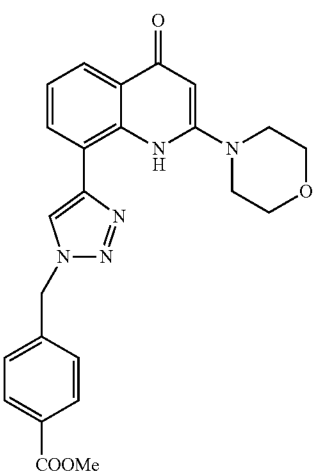 [SMILES: COC(=O)c1ccc(Cn2cc(-c3cccc4c(=O)cc(N5CCOCC5)[nH]c34)nn2)cc1] |
| 2-((4-(2-morpholino-4-oxo-1,4-dihydroquinolin-8-yl)-1H-1,2,3-triazol-1-yl)methyl)benzonitrile | 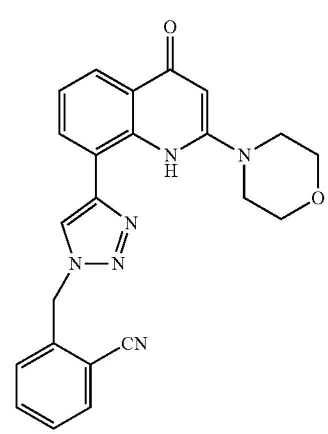 [SMILES: N#Cc1ccccc1Cn1cc(-c2cccc3c(=O)cc(N4CCOCC4)[nH]c23)nn1] |

TABLE 1-continued

| Name | Structure |
|---|---|
| methyl 3-((4-(2-morpholino-4-oxo-1,4-dihydroquinolin-8-yl)-1H-1,2,3-triazol-1-yl)methyl)benzoate | 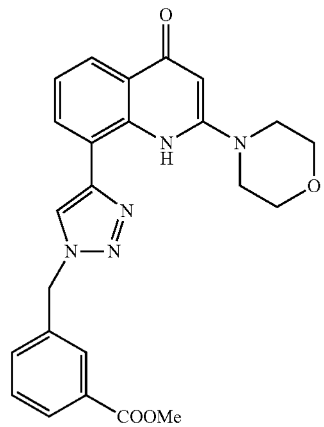 [SMILES: COC(=O)c1cccc(Cn2cc(-c3cccc4c(=O)cc(N5CCOCC5)[nH]c34)nn2)c1] |
| 8-(1-(2-(1H-indol-3-yl)ethyl)-1H-1,2,3-triazol-4-yl)-2-morpholinoquinolin-4(1H)-one | 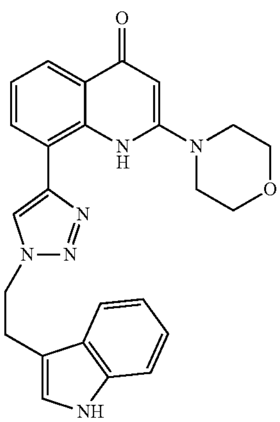 [SMILES: O=c1cc(N2CCOCC2)[nH]c2c(-c3cn(CCc4c[nH]c5ccccc45)nn3)cccc12] |
| 3-((4-(2-morpholino-4-oxo-1,4-dihydroquinolin-8-yl)-1H-1,2,3-triazol-1-yl)methyl)benzoic acid | 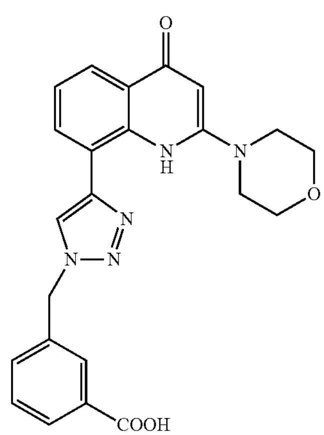 [SMILES: O=C(O)c1cccc(Cn2cc(-c3cccc4c(=O)cc(N5CCOCC5)[nH]c34)nn2)c1] |

TABLE 1-continued

| Name | Structure |
|---|---|
| 8-(1-(4-methoxyphenyl)-1H-1,2,3-triazol-4-yl)-2-morpholinoquinolin-4(1H)-one | 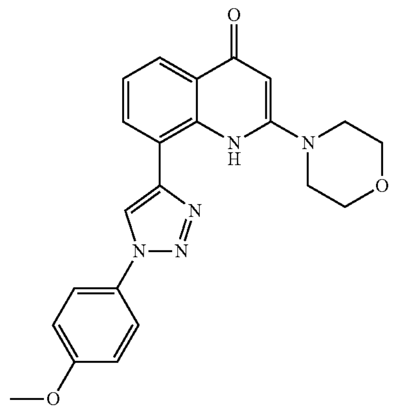 [SMILES: COc1ccc(-n2cc(-c3cccc4c(=O)cc(N5CCOCC5)[nH]c34)nn2)cc1] |
| 4-(4-(2-morpholino-4-oxo-1,4-dihydroquinolin-8-yl)-1H-1,2,3-triazol-1-yl)benzoic acid | 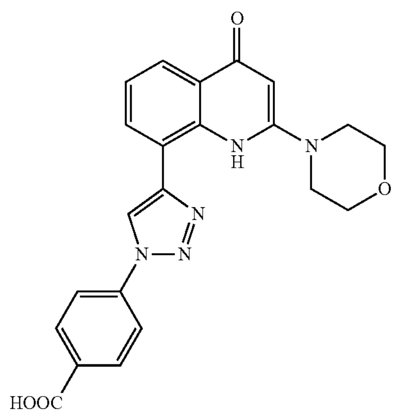 [SMILES: O=C(O)c1ccc(-n2cc(-c3cccc4c(=O)cc(N5CCOCC5)[nH]c34)nn2)cc1] |
| 8-(1-(3-hydroxyphenyl)-1H-1,2,3-triazol-4-yl)-2-morpholinoquinolin-4(1H)-one | 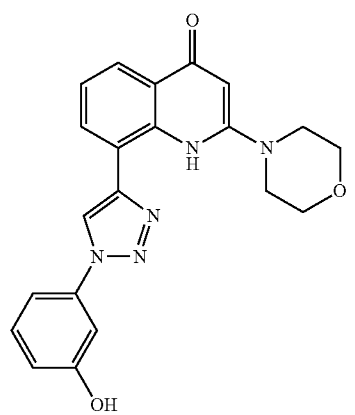 [SMILES: O=c1cc(N2CCOCC2)[nH]c2c(-c3cn(-c4cccc(O)c4)nn3)cccc12] |

TABLE 1-continued

| Name | Structure |
|---|---|
| 8-(1-(3-hydroxy-4-methoxyphenyl)-1H-1,2,3-triazol-4-yl)-2-morpholinoquinolin-4(1H)-one | 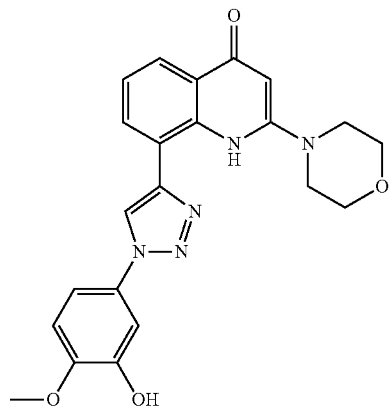 [SMILES: COc1ccc(-n2cc(-c3cccc4c(=O)cc(N5CCOCC5)[nH]c34)nn2)cc1O] |
| 8-(1-(4-chlorophenyl)-1H-1,2,3-triazol-4-yl)-2-morpholinoquinolin-4(1H)-one | 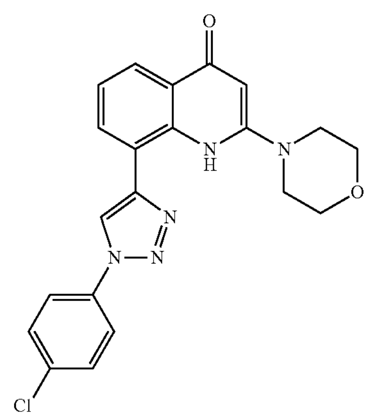 [SMILES: O=c1cc(N2CCOCC2)[nH]c2c(-c3cn(-c4ccc(Cl)cc4)nn3)cccc12] |
| 8-(1-(4-methoxy-3-nitrophenyl)-1H-1,2,3-triazol-4-yl)-2-morpholinoquinolin-4(1H)-one | 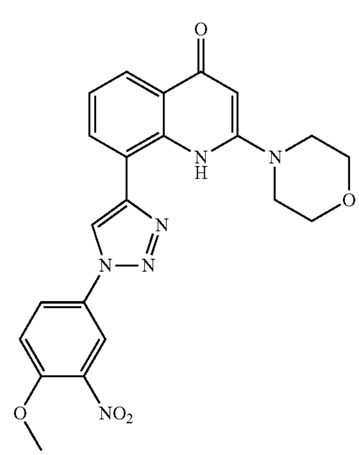 [SMILES: COc1ccc(-n2cc(-c3cccc4c(=O)cc(N5CCOCC5)[nH]c34)nn2)cc1[N+](=O)[O-]] |

TABLE 1-continued

| Name | Structure |
|---|---|
| 8-(1-(3,5-dimethoxyphenyl)-1H-1,2,3-triazol-4-yl)-2-morpholinoquinolin-4(1H)-one | 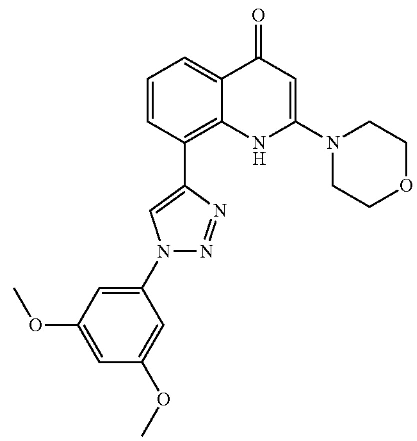 [SMILES: COc1cc(OC)cc(-n2cc(-c3cccc4c(=O)cc(N5CCOCC5)[nH]c34)nn2)c1] |
| methyl 4-(4-(2-morpholino-4-oxo-1,4-dihydroquinolin-8-yl)-1H-1,2,3-triazol-1-yl)benzoate | 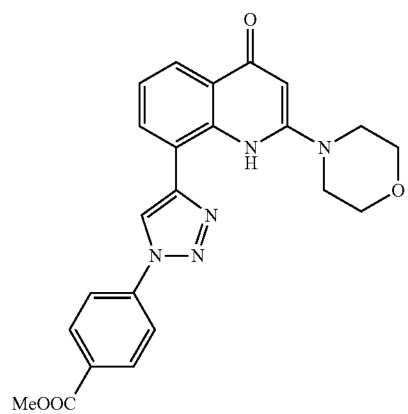 [SMILES: COC(=O)c1ccc(-n2cc(-c3cccc4c(=O)cc(N5CCOCC5)[nH]c34)nn2)cc1] |
| 8-(1-(benzo[d][1,3]dioxol-5-yl)-1H-1,2,3-triazol-4-yl)-2-morpholinoquinolin-4(1H)-one | 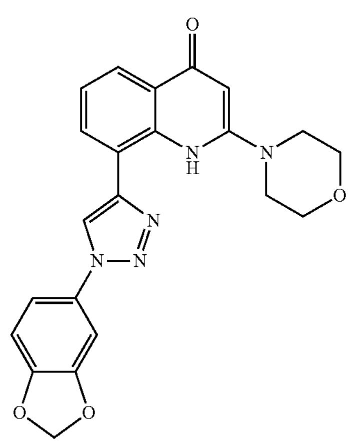 [SMILES: O=c1cc(N2CCOCC2)[nH]c2c(-c3cn(-c4ccc5c(c4)OCO5)nn3)cccc12] |

TABLE 1-continued

| Name | Structure |
|---|---|
| N-(4-methoxy-3-(4-(2-morpholino-4-oxo-1,4-dihydroquinolin-8-yl)-1H-1,2,3-triazol-1-yl)phenyl)acetamide | 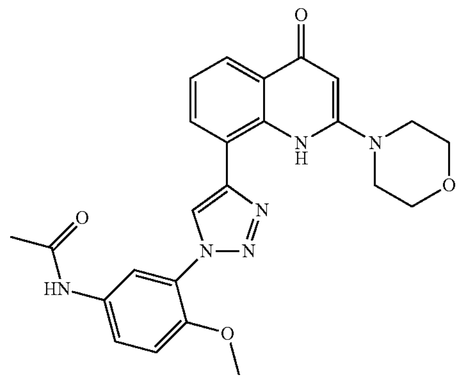 [SMILES: COc1ccc(NC(C)=O)cc1-n1cc(-c2cccc3c(=O)cc(N4CCOCC4)[nH]c23)nn1] |
| 8-(1-(4-hydroxy-2-methylphenyl)-1H-1,2,3-triazol-4-yl)-2-morpholinoquinolin-4(1H)-one | 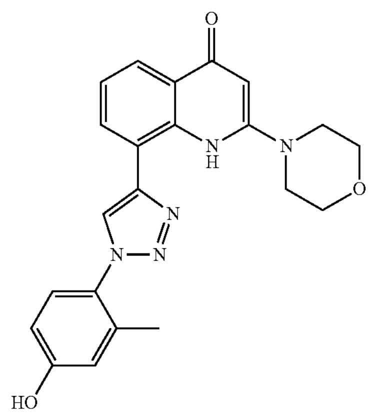 [SMILES: Cc1cc(O)ccc1-n1cc(-c2cccc3c(=O)cc(N4CCOCC4)[nH]c23)nn1] |
| 2-morpholino-8-(1-(quinolin-3-yl)-1H-1,2,3-triazol-4-yl)quinolin-4(1H)-one | 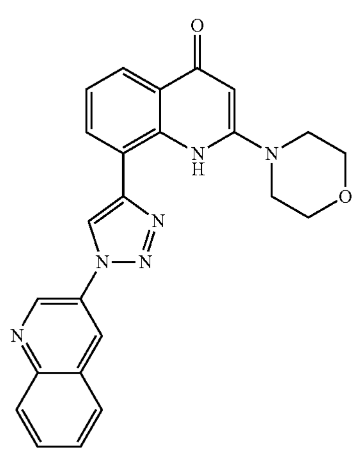 [SMILES: O=c1cc(N2CCOCC2)[nH]c2c(-c3cn(-c4cnc5ccccc5c4)nn3)cccc12] |

TABLE 1-continued

| Name | Structure |
|---|---|
| 2-morpholino-8-(1-(4-(trifluoromethoxy)phenyl)-1H-1,2,3-triazol-4-yl)quinolin-4(1H)-one | 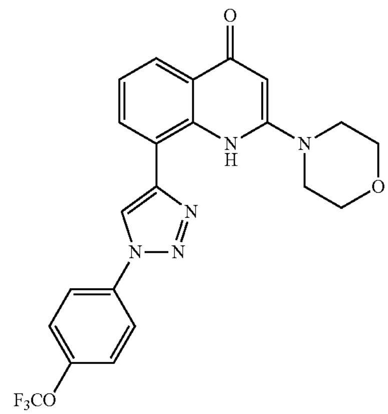 [SMILES: O=c1cc(N2CCOCC2)[nH]c2c(-c3cn(-c4ccc(OC(F)(F)F)cc4)nn3)cccc12] |
| 2-morpholino-8-(1-(naphthalen-1-yl)-1H-1,2,3-triazol-4-yl)quinolin-4(1H)-one | 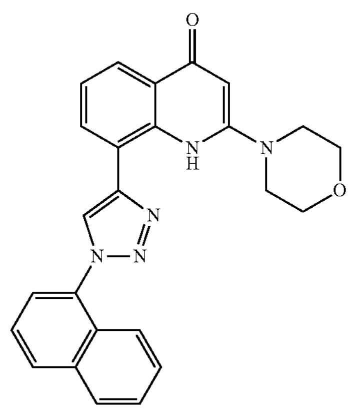 [SMILES: O=c1cc(N2CCOCC2)[nH]c2c(-c3cn(-c4cccc5ccccc45)nn3)cccc12] |
| 2-morpholino-8-(1-(naphthalen-2-yl)-1H-1,2,3-triazol-4-yl)quinolin-4(1H)-one | 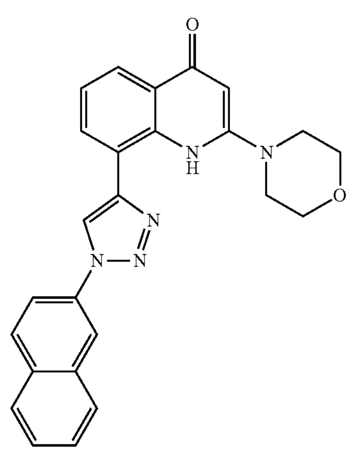 [SMILES: O=c1cc(N2CCOCC2)[nH]c2c(-c3cn(-c4ccc5ccccc5c4)nn3)cccc12] |

TABLE 1-continued

| Name | Structure |
|---|---|
| 8-(1-(4-aminophenyl)-1H-1,2,3-triazol-4-yl)-2-morpholinoquinolin-4(1H)-one | 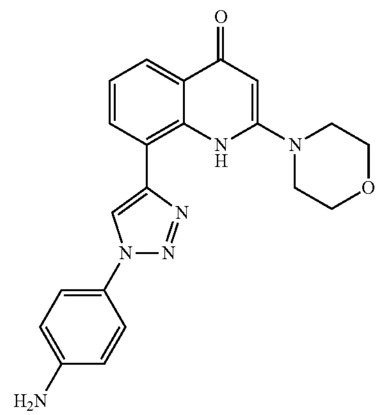 [SMILES: Nc1ccc(-n2cc(-c3cccc4c(=O)cc(N5CCOCC5)[nH]c34)nn2)cc1] |
| 8-(1-(3-methoxy-5-(trifluoromethoxy)phenyl)-1H-1,2,3-triazol-4-yl)-2-morpholinoquinolin-4(1H)-one | 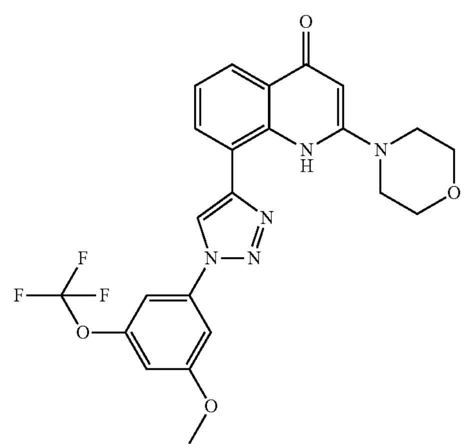 [SMILES: COc1cc(OC(F)(F)F)cc(-n2cc(-c3cccc4c(=O)cc(N5CCOCC5)[nH]c34)nn2)c1] |
| 8-(1-(2-methoxyphenyl)-1H-1,2,3-triazol-4-yl)-2-morpholinoquinolin-4(1H)-one | 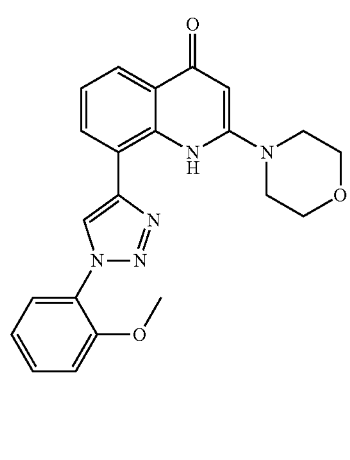 [SMILES: COc1ccccc1-n1cc(-c2cccc3c(=O)cc(N4CCOCC4)[nH]c23)nn1] |

TABLE 1-continued

| Name | Structure |
|---|---|
| 3-(4-(2-morpholino-4-oxo-1,4-dihydroquinolin-8-yl)-1H-1,2,3-triazol-1-yl)benzoic acid | 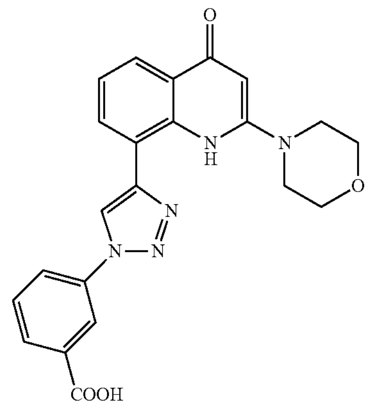 [SMILES: O=C(O)c1cccc(-n2cc(-c3cccc4c(=O)cc(N5CCOCC5)[nH]c34)nn2)c1] |
| 8-(1-(3,4-dimethoxyphenyl)-1H-1,2,3-triazol-4-yl)-2-morpholinoquinolin-4(1H)-one | 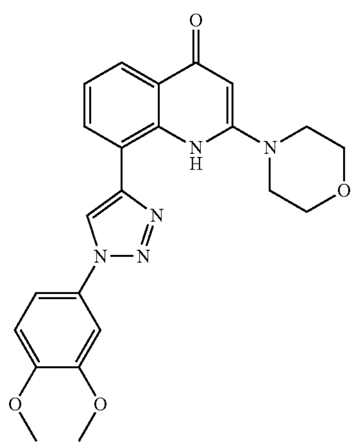 [SMILES: COc1ccc(-n2cc(-c3cccc4c(=O)cc(N5CCOCC5)[nH]c34)nn2)cc1OC] |
| 4-(4-(2-morpholino-4-oxo-1,4-dihydroquinolin-8-yl)-1H-1,2,3-triazol-1-yl)butanoic acid | 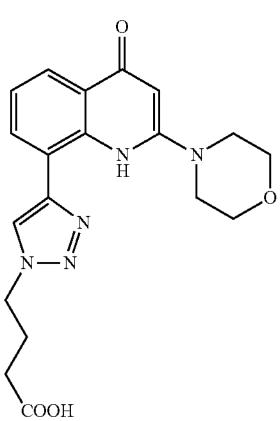 [SMILES: O=C(O)CCCn1cc(-c2cccc3c(=O)cc(N4CCOCC4)[nH]c23)nn1] |

TABLE 1-continued

| Name | Structure |
|---|---|
| methyl 3-(4-(2-morpholino-4-oxo-1,4-dihydroquinolin-8-yl)-1H-1,2,3-triazol-1-yl)benzoate | 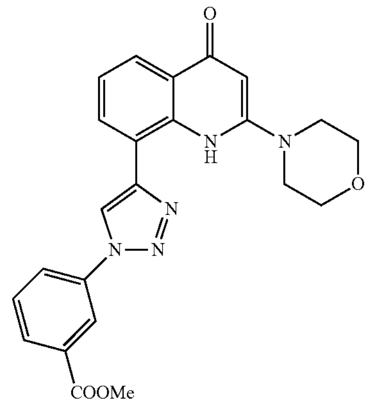 [SMILES: COC(=O)c1cccc(-n2cc(-c3cccc4c(=O)cc(N5CCOCC5)[nH]c34)nn2)c1] |
| 5-(4-(2-morpholino-4-oxo-1,4-dihydroquinolin-8-yl)-1H-1,2,3-triazol-1-yl)pentanoic acid | 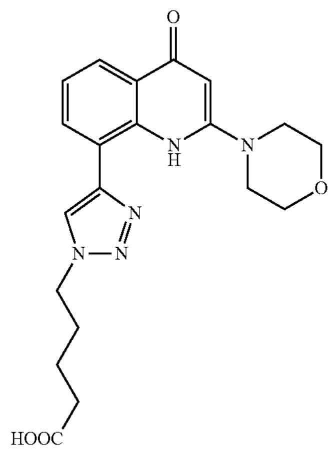 [SMILES: O=C(O)CCCCn1cc(-c2cccc3c(=O)cc(N4CCOCC4)[nH]c23)nn1] |
| 6-(4-(2-morpholino-4-oxo-1,4-dihydroquinolin-8-yl)-1H-1,2,3-triazol-1-yl)hexanoic acid | 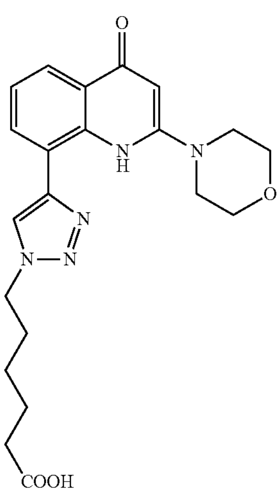 [SMILES: O=C(O)CCCCCn1cc(-c2cccc3c(=O)cc(N4CCOCC4)[nH]c23)nn1] |

TABLE 1-continued

| Name | Structure |
| --- | --- |
| 4-methyl-N-(3-((4-(2-morpholino-4-oxo-1,4-dihydroquinolin-8-yl)-1H-1,2,3-triazol-1-yl)methyl)phenyl)benzenesulfonamide | 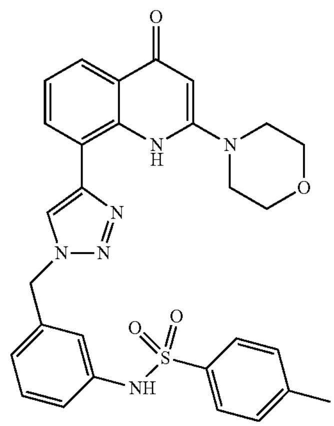 [SMILES: Cc1ccc(S(=O)(=O)Nc2cccc(Cn3cc(-c4cccc5c(=O)cc(N6CCOCC6)[nH]c45)nn3)c2)cc1] |
| 4-(4-(2-morpholino-4-oxo-1,4-dihydroquinolin-8-yl)-1H-1,2,3-triazol-1-yl)benzenesulfonamide | 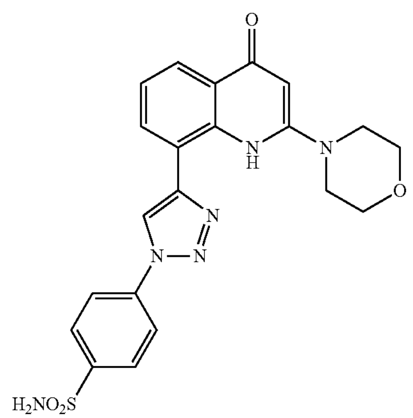 [SMILES: NS(=O)(=O)c1ccc(-n2cc(-c3cccc4c(=O)cc(N5CCOCC5)[nH]c34)nn2)cc1] |
| 4-(4-(2-morpholino-4-oxo-1,4-dihydroquinolin-8-yl)-1H-1,2,3-triazol-1-yl)-N-(phenylsulfonyl)benzamide | 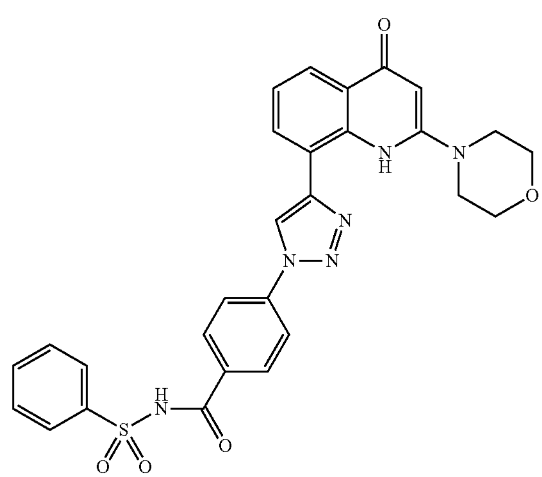 [SMILES: O=C(NS(=O)(=O)c1ccccc1)c1ccc(-n2cc(-c3cccc4c(=O)cc(N5CCOCC5)[nH]c34)nn2)cc1] |

TABLE 1-continued

| Name | Structure |
| --- | --- |
| 8-(1-(3-(1H-tetrazol-5-yl)benzyl)-1H-1,2,3-triazol-4-yl)-2-morpholinoquinolin-4(1H)-one | 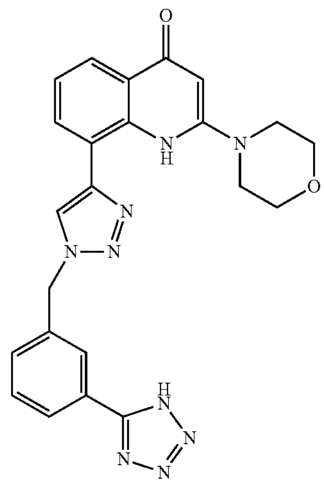 [SMILES: O=c1cc(N2CCOCC2)[nH]c2c(-c3cn(Cc4cccc(-c5nnn[nH]5)c4)nn3)cccc12] |
| 8-(1-(4-(1H-tetrazol-5-yl)phenyl)-1H-1,2,3-triazol-4-yl)-2-morpholinoquinolin-4(1H)-one | 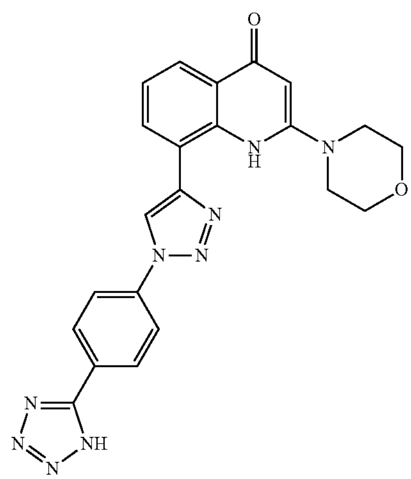 [SMILES: O=c1cc(N2CCOCC2)[nH]c2c(-c3cn(-c4ccc(-c5nnn[nH]5)cc4)nn3)cccc12] |
| N-benzyl-3-((4-(2-morpholino-4-oxo-1,4-dihydroquinolin-8-yl)-1H-1,2,3-triazol-1-yl)methyl)benzamide | 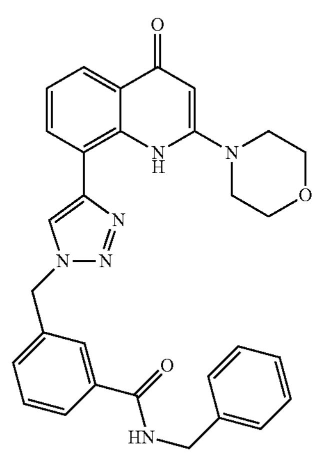 |

TABLE 1-continued

| Name | Structure |
|---|---|
| N,N-diethyl-3-((4-(2-morpholino-4-oxo-1,4-dihydroquinolin-8-yl)-1H-1,2,3-triazol-1-yl)methyl)benzamide | 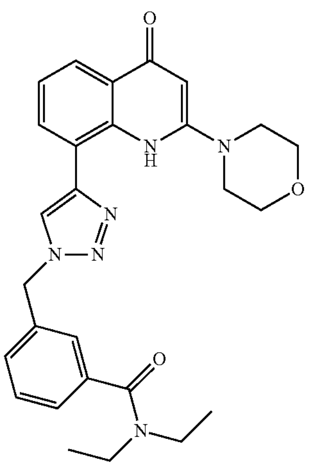 [SMILES: CCN(CC)C(=O)c1cccc(Cn2cc(-c3cccc4c(=O)cc(N5CCOCC5)[nH]c34)nn2)c1] |
| N-cyclopropyl-3-((4-(2-morpholino-4-oxo-1,4-dihydroquinolin-8-yl)-1H-1,2,3-triazol-1-yl)methyl)benzamide | 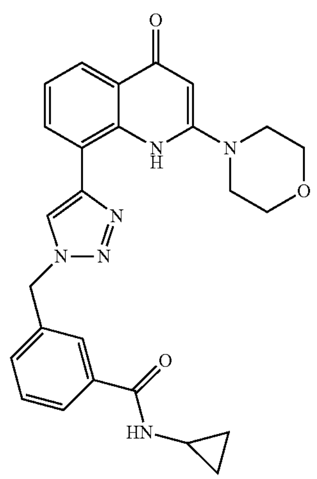 [SMILES: O=C(NC1CC1)c1cccc(Cn2cc(-c3cccc4c(=O)cc(N5CCOCC5)[nH]c34)nn2)c1] |
| N-methyl-4-(4-(2-morpholino-4-oxo-1,4-dihydroquinolin-8-yl)-1H-1,2,3-triazol-1-yl)-N-(phenylsulfonyl)benzamide | 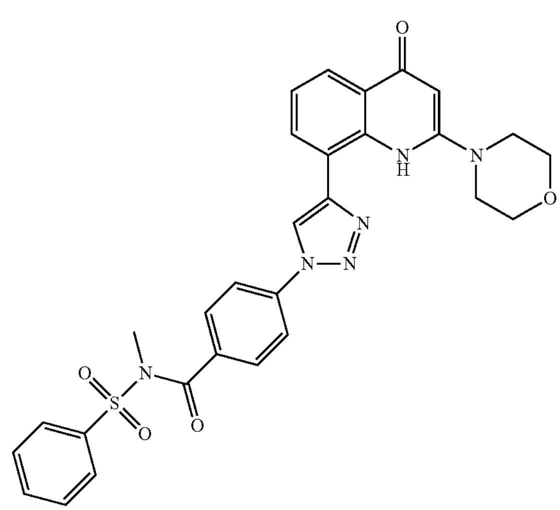 [SMILES: CN(C(=O)c1ccc(-n2cc(-c3cccc4c(=O)cc(N5CCOCC5)[nH]c34)nn2)cc1)S(=O)(=O)c1ccccc1] |

TABLE 1-continued
| Name | Structure |
|---|---|
| benzyl 3-((4-(2-morpholino-4-oxo-1,4-dihydroquinolin-8-yl)-1H-1,2,3-triazol-1-yl)methyl)benzoate | 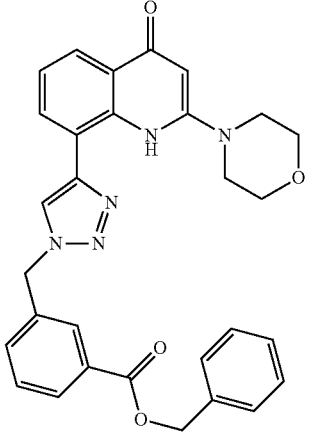 [SMILES: O=C(OCc1ccccc1)c1cccc(Cn2cc(-c3cccc4c(=O)cc(N5CCOCC5)[nH]c34)nn2)c1] |
| isopropyl 3-((4-(2-morpholino-4-oxo-1,4-dihydroquinolin-8-yl)-1H-1,2,3-triazol-1-yl)methyl)benzoate | 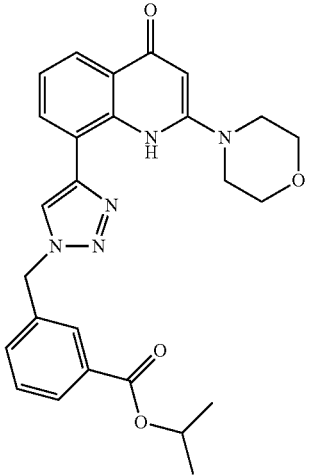 [SMILES: CC(C)OC(=O)c1cccc(Cn2cc(-c3cccc4c(=O)cc(N5CCOCC5)[nH]c34)nn2)c1] |
| ethyl 3-((4-(2-morpholino-4-oxo-1,4-dihydroquinolin-8-yl)-1H-1,2,3-triazol-1-yl)methyl)benzoate | 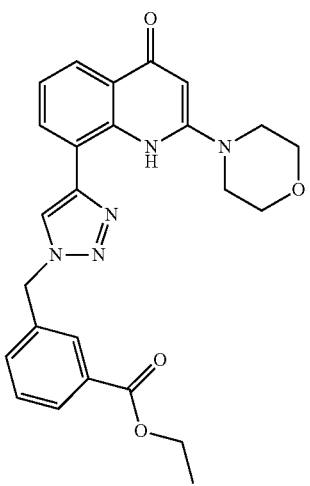 [SMILES: CCOC(=O)c1cccc(Cn2cc(-c3cccc4c(=O)cc(N5CCOCC5)[nH]c34)nn2)c1] |

TABLE 1-continued
| Name | Structure |
|---|---|
| pyridin-4-ylmethyl 3-((4-(2-morpholino-4-oxo-1,4-dihydroquinolin-8-yl)-1H-1,2,3-triazol-1-yl)methyl)benzoate | 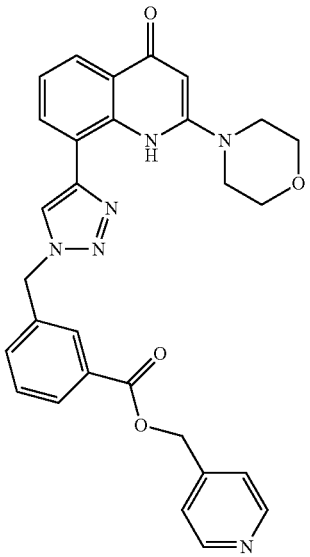 [SMILES: O=C(OCc1ccncc1)c1cccc(Cn2cc(-c3cccc4c(=O)cc(N5CCOCC5)[nH]c34)nn2)c1] |
| methyl 2-((4-(2-morpholino-4-oxo-1,4-dihydroquinolin-8-yl)-1H-1,2,3-triazol-1-yl)methyl)isonicotinate | 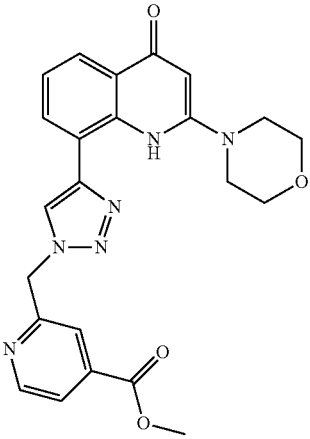 [SMILES: COC(=O)c1ccnc(Cn2cc(-c3cccc4c(=O)cc(N5CCOCC5)[nH]c34)nn2)c1] |
| 2-((4-(2-morpholino-4-oxo-1,4-dihydroquinolin-8-yl)-1H-1,2,3-triazol-1-yl)methyl)isonicotinic acid | 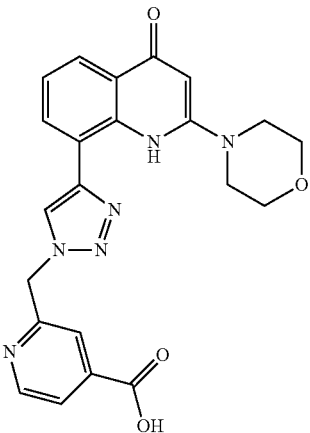 [SMILES: O=C(O)c1ccnc(Cn2cc(-c3cccc4c(=O)cc(N5CCOCC5)[nH]c34)nn2)c1] |

TABLE 1-continued
| Name | Structure |
|---|---|
| methyl 3-((4-(1-methyl-2-morpholino-4-oxo-1,4-dihydroquinolin-8-yl)-1H-1,2,3-triazol-1-yl)methyl)benzoate | 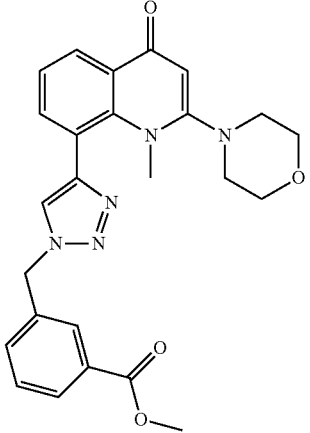 [SMILES: COC(=O)c1cccc(Cn2cc(-c3cccc4c(=O)cc(N5CCOCC5)n(C)c34)nn2)c1] |
| 8-(1-(2-hydroxyphenyl)-1H-1,2,3-triazol-4-yl)-1-methyl-2-morpholinoquinolin-4(1H)-one | 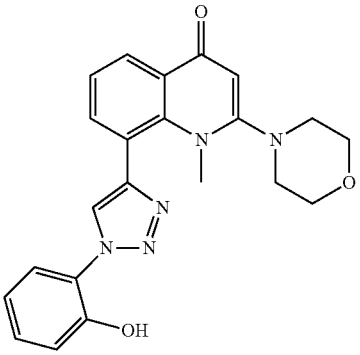 [SMILES: Cn1c(N2CCOCC2)cc(=O)c2cccc(-c3cn(-c4ccccc4O)nn3)c21] |
| 3-((4-(1-methyl-2-morpholino-4-oxo-1,4-dihydroquinolin-8-yl)-1H-1,2,3-triazol-1-yl)methyl)benzoic acid | 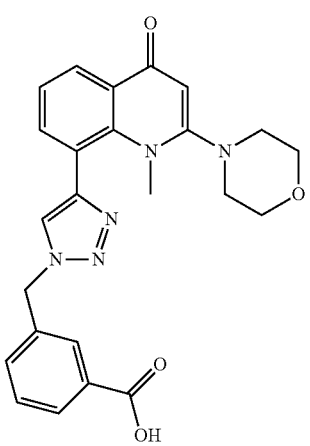 [SMILES: Cn1c(N2CCOCC2)cc(=O)c2cccc(-c3cn(Cc4cccc(C(=O)O)c4)nn3)c21] |

TABLE 1-continued

| Name | Structure |
|---|---|
| benzyl 3-((4-(1-methyl-2-morpholino-4-oxo-1,4-dihydroquinolin-8-yl)-1H-1,2,3-triazol-1-yl)methyl)benzoate | 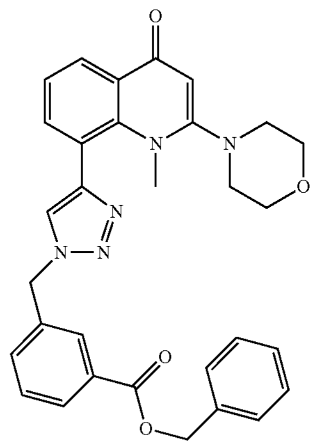 [SMILES: Cn1c(N2CCOCC2)cc(=O)c2cccc(-c3cn(Cc4cccc(C(=O)OCc5ccccc5)c4)nn3)c21] |
| ethyl 3-((4-(1-methyl-2-morpholino-4-oxo-1,4-dihydroquinolin-8-yl)-1H-1,2,3-triazol-1-yl)methyl)benzoate | 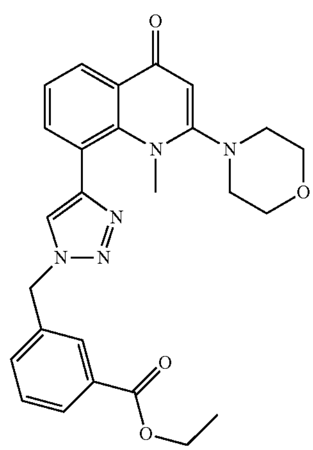 [SMILES: CCOC(=O)c1cccc(Cn2cc(-c3cccc4c(=O)cc(N5CCOCC5)n(C)c34)nn2)c1] |
| butyl 3-((4-(2-morpholino-4-oxo-1,4-dihydroquinolin-8-yl)-1H-1,2,3-triazol-1-yl)methyl)benzoate | 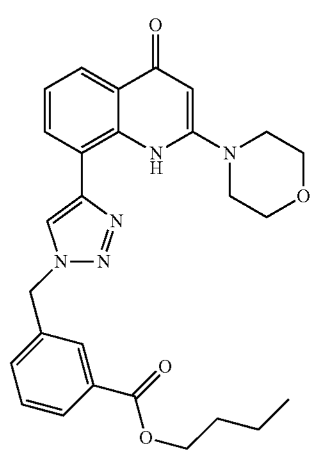 [SMILES: CCCCOC(=O)c1cccc(Cn2cc(-c3cccc4c(=O)cc(N5CCOCC5)[nH]c34)nn2)c1] |

TABLE 1-continued
| Name | Structure |
|---|---|
| 2-morpholinoethyl 3-((4-(2-morpholino-4-oxo-1,4-dihydroquinolin-8-yl)-1H-1,2,3-triazol-1-yl)methyl)benzoate | 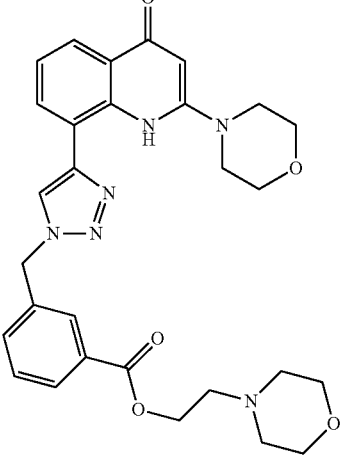 |
| isopentyl 3-((4-(2-morpholino-4-oxo-1,4-dihydroquinolin-8-yl)-1H-1,2,3-triazol-1-yl)methyl)benzoate | 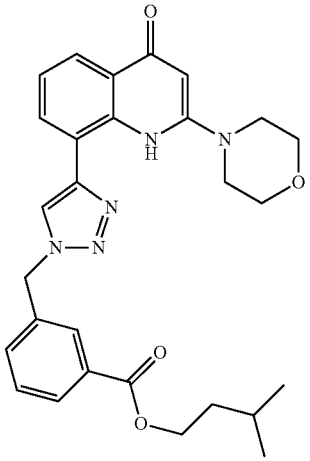 [SMILES: CC(C)CCOC(=O)c1cccc(Cn2cc(-c3cccc4c(=O)cc(N5CCOCC5)[nH]c34)nn2)c1] |
| pivaloyloxymethyl 3-((4-(2-morpholino-4-oxo-1,4-dihydroquinolin-8-yl)-1H-1,2,3-triazol-1-yl)methyl)benzoate | 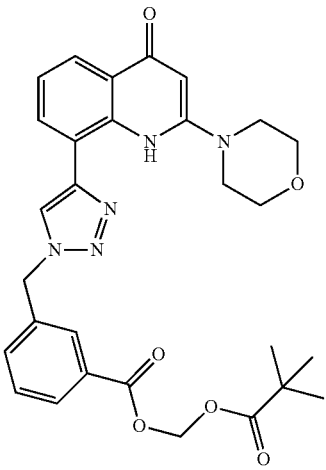 [SMILES: CC(C)(C)C(=O)OCOC(=O)c1cccc(Cn2cc(-c3cccc4c(=O)cc(N5CCOCC5)[nH]c34)nn2)c1] |

TABLE 1-continued

| Name | Structure |
|---|---|
| 1-(pivaloyloxy)ethyl 3-((4-(2-morpholino-4-oxo-1,4-dihydroquinolin-8-yl)-1H-1,2,3-triazol-1-yl)methyl)benzoate | 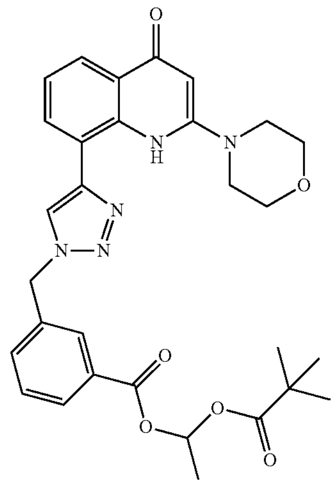 [SMILES: CC(OC(=O)c1cccc(Cn2cc(-c3cccc4c(=O)cc(N5CCOCC5)[nH]c34)nn2)c1)OC(=O)C(C)(C)C] |
| 1-(tert-butoxycarbonyloxy)ethyl 3-((4-(2-morpholino-4-oxo-1,4-dihydroquinolin-8-yl)-1H-1,2,3-triazol-1-yl)methyl)benzoate | 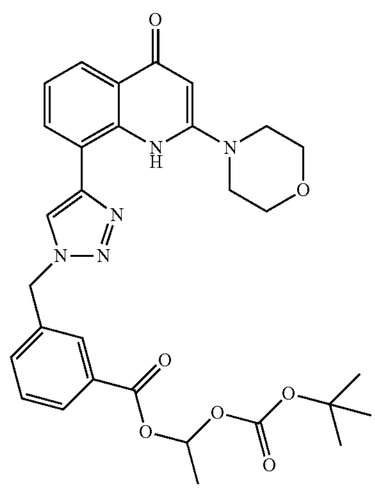 [SMILES: CC(OC(=O)OC(C)(C)C)OC(=O)c1cccc(Cn2cc(-c3cccc4c(=O)cc(N5CCOCC5)[nH]c34)nn2)c1] |
| 1-(cyclohexyloxycarbonyloxy)ethyl 3-((4-(2-morpholino-4-oxo-1,4-dihydroquinolin-8-yl)-1H-1,2,3-triazol-1-yl)methyl)benzoate | 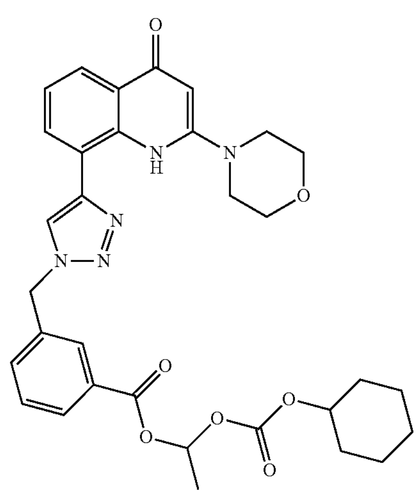 [SMILES: CC(OC(=O)OC1CCCCC1)OC(=O)c1cccc(Cn2cc(-c3cccc4c(=O)cc(N5CCOCC5)[nH]c34)nn2)c1] |

TABLE 1-continued

| Name | Structure |
|---|---|
| 2-morpholino-8-(1-((1-oxo-1,3-dihydroisobenzofuran-4-yl)methyl)-1H-1,2,3-triazol-4-yl)quinolin-4(1H)-one | 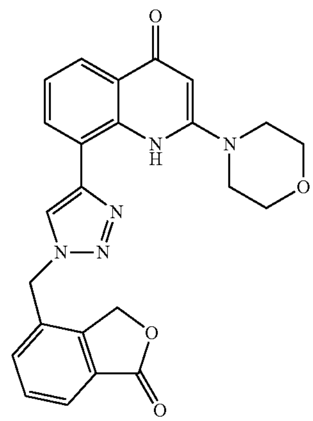 [SMILES: O=C1OCc2c(Cn3cc(-c4cccc5c(=O)cc(N6CCOCC6)[nH]c45)nn3)cccc21] |
| 2-morpholino-8-(1-((1-oxoisochroman-5-yl)methyl)-1H-1,2,3-triazol-4-yl)quinolin-4(1H)-one | 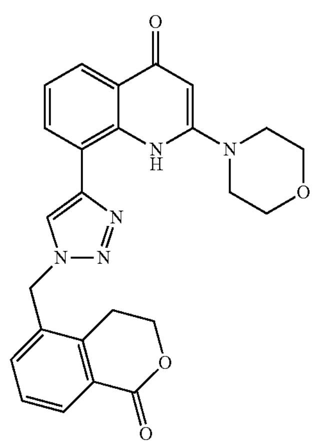 [SMILES: O=C1OCCc2c(Cn3cc(-c4cccc5c(=O)cc(N6CCOCC6)[nH]c45)nn3)cccc21] |
| heptyl 3-((4-(2-morpholino-4-oxo-1,4-dihydroquinolin-8-yl)-1H-1,2,3-triazol-1-yl)methyl)benzoate | 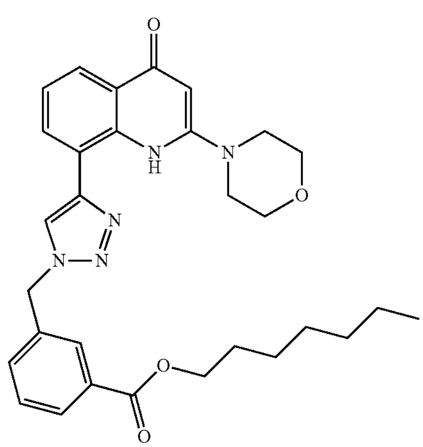 [SMILES: CCCCCCCOC(=O)c1cccc(Cn2cc(-c3cccc4c(=O)cc(N5CCOCC5)[nH]c34)nn2)c1] |

TABLE 1-continued
| Name | Structure |
|---|---|
| undecyl 3-((4-(2-morpholino-4-oxo-1,4-dihydroquinolin-8-yl)-1H-1,2,3-triazol-1-yl)methyl)benzoate | 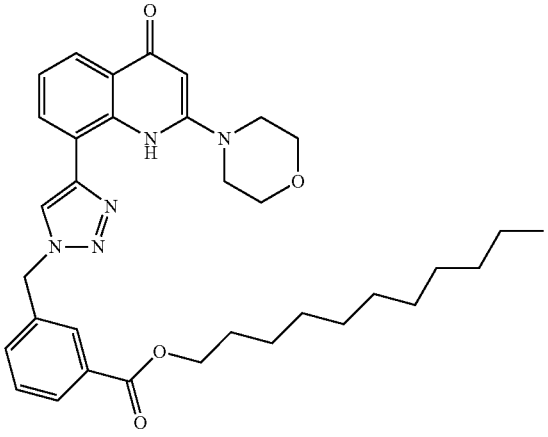 [SMILES: CCCCCCCCCCCOC(=O)c1cccc(Cn2cc(-c3cccc4c(=O)cc(N5CCOCC5)[nH]c34)nn2)c1] |
| octadecyl 3-((4-(2-morpholino-4-oxo-1,4-dihydroquinolin-8-yl)-1H-1,2,3-triazol-1-yl)methyl)benzoate | 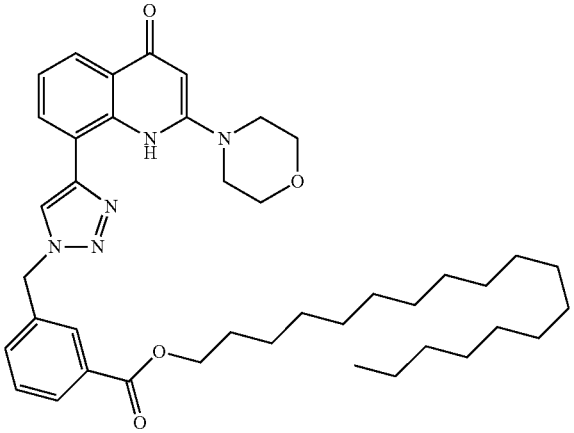 [SMILES: CCCCCCCCCCCCCCCCCCOC(=O)c1cccc(Cn2cc(-c3cccc4c(=O)cc(N5CCOCC5)[nH]c34)nn2)c1] |
| 8-(1-benzyl-1H-1,2,3-triazol-4-yl)-2-(1,4-oxazepan-4-yl)quinolin-4(1H)-one | 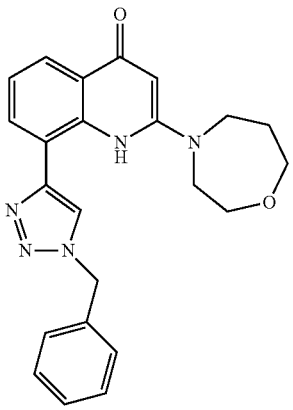 [SMILES: O=c1cc(N2CCCOCC2)[nH]c2c(-c3cn(Cc4ccccc4)nn3)cccc12] |

TABLE 1-continued

| Name | Structure |
|---|---|
| 2-(1,4-oxazepan-4-yl)-8-(1-phenyl-1H-1,2,3-triazol-4-yl)quinolin-4(1H)-one | 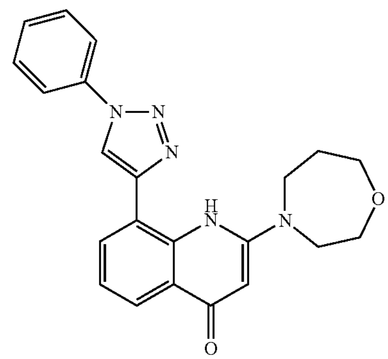 [SMILES: O=c1cc(N2CCCOCC2)[nH]c2c(-c3cn(-c4ccccc4)nn3)cccc12] |
| 2-(4-(4-(2-(1,4-oxazepan-4-yl)-4-oxo-1,4-dihydroquinolin-8-yl)-1H-1,2,3-triazol-1-yl)phenyl)acetonitrile | 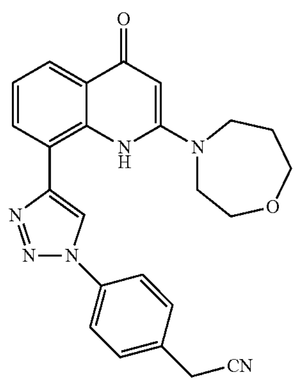 [SMILES: N#CCc1ccc(-n2cc(-c3cccc4c(=O)cc(N5CCCOCC5)[nH]c34)nn2)cc1] |
| 8-(1-(3-methoxyphenyl)-1H-1,2,3-triazol-4-yl)-2-(1,4-oxazepan-4-yl)quinolin-4(1H)-one | 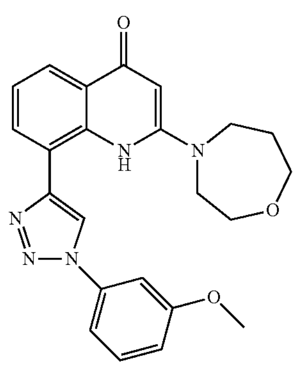 [SMILES: COc1cccc(-n2cc(-c3cccc4c(=O)cc(N5CCCOCC5)[nH]c34)nn2)c1] |
| 2-(1,4-oxazepan-4-yl)-8-(1-(pyridin-4-yl)-1H-1,2,3-triazol-4-yl)quinolin-4(1H)-one | 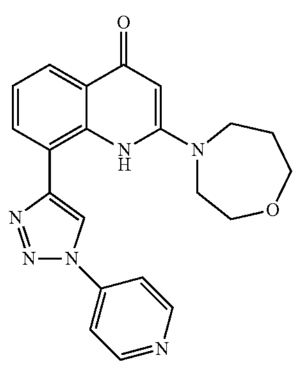 [SMILES: O=c1cc(N2CCCOCC2)[nH]c2c(-c3cn(-c4ccncc4)nn3)cccc12] |

TABLE 1-continued

| Name | Structure |
|---|---|
| 8-(1-(2-hydroxyphenyl)-1H-1,2,3-triazol-4-yl)-2-(1,4-oxazepan-4-yl)quinolin-4(1H)-one | 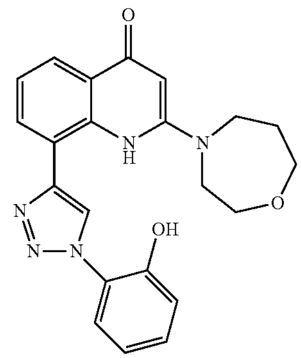 [SMILES: O=c1cc(N2CCCOCC2)[nH]c2c(-c3cn(-c4ccccc4O)nn3)cccc12] |
| 8-(1-(4-(benzyloxy)phenyl)-1H-1,2,3-triazol-4-yl)-2-(1,4-oxazepan-4-yl)quinolin-4(1H)-one | 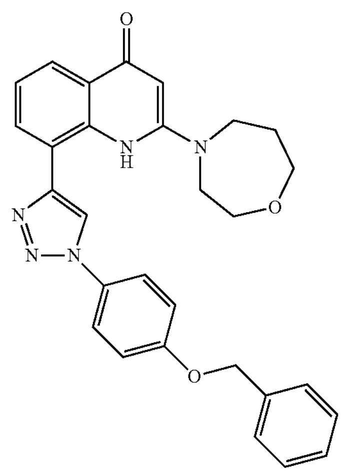 [SMILES: O=c1cc(N2CCCOCC2)[nH]c2c(-c3cn(-c4ccc(OCc5ccccc5)cc4)nn3)cccc12] |
| methyl 4-((4-(2-(1,4-oxazepan-4-yl)-4-oxo-1,4-dihydroquinolin-8-yl)-1H-1,2,3-triazol-1-yl)methyl)benzoate | 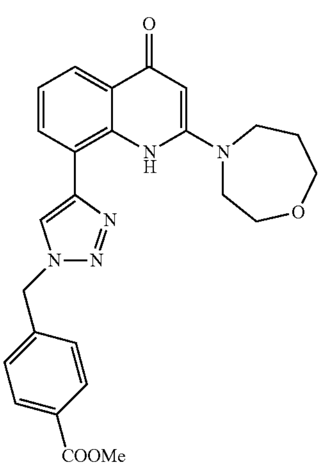 [SMILES: COC(=O)c1ccc(Cn2cc(-c3cccc4c(=O)cc(N5CCCOCC5)[nH]c34)nn2)cc1] |

TABLE 1-continued

| Name | Structure |
| --- | --- |
| 2-((4-(2-(1,4-oxazepan-4-yl)-4-oxo-1,4-dihydroquinolin-8-yl)-1H-1,2,3-triazol-1-yl)methyl)benzonitrile | 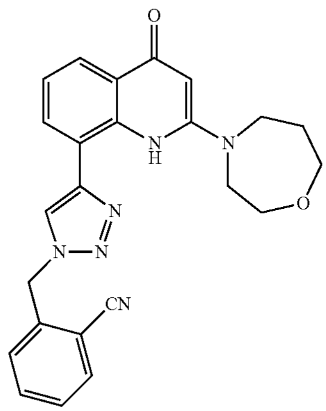 [SMILES: N#Cc1ccccc1Cn1cc(-c2cccc3c(=O)cc(N4CCCOCC4)[nH]c23)nn1] |
| methyl 3-((4-(2-(1,4-oxazepan-4-yl)-4-oxo-1,4-dihydroquinolin-8-yl)-1H-1,2,3-triazol-1-yl)methyl)benzoate | 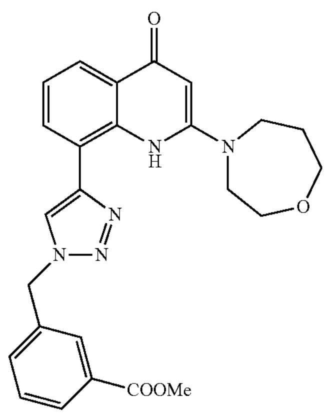 [SMILES: COC(=O)c1cccc(Cn2cc(-c3cccc4c(=O)cc(N5CCCOCC5)[nH]c34)nn2)c1] |
| 8-(1-(2-(1H-indol-3-yl)ethyl)-1H-1,2,3-triazol-4-yl)-2-(1,4-oxazepan-4-yl)quinolin-4(1H)-one | 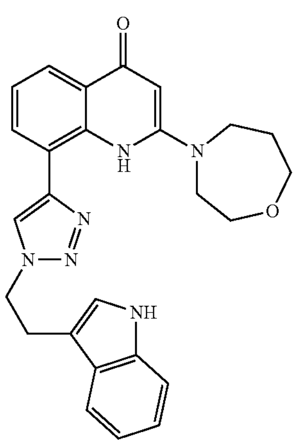 [SMILES: O=c1cc(N2CCCOCC2)[nH]c2c(-c3cn(CCc4c[nH]c5ccccc45)nn3)cccc12] |

TABLE 1-continued

| Name | Structure |
|---|---|
| 3-((4-(2-(1,4-oxazepan-4-yl)-4-oxo-1,4-dihydroquinolin-8-yl)-1H-1,2,3-triazol-1-yl)methyl)benzoic acid | 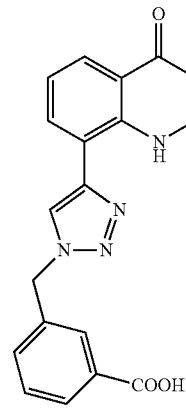 |
| 8-(1-(4-methoxyphenyl)-1H-1,2,3-triazol-4-yl)-2-(1,4-oxazepan-4-yl)quinolin-4(1H)-one | 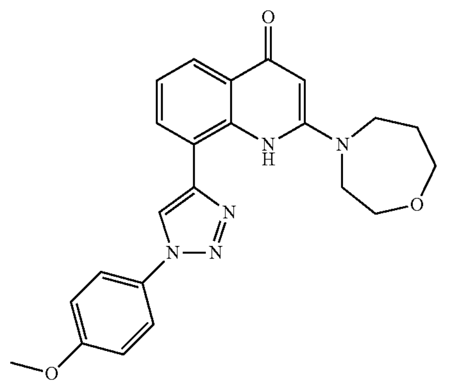 [SMILES: COc1ccc(-n2cc(-c3cccc4c(=O)cc(N5CCCOCC5)[nH]c34)nn2)cc1] |
| 4-(4-(2-(1,4-oxazepan-4-yl)-4-oxo-1,4-dihydroquinolin-8-yl)-1H-1,2,3-triazol-1-yl)benzoic acid | 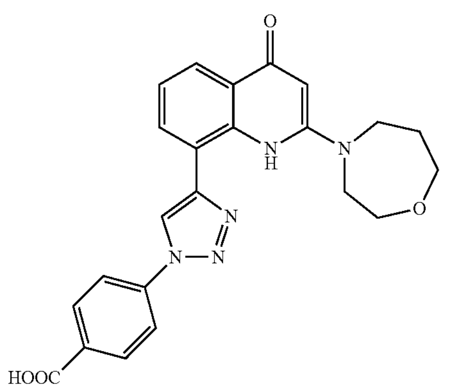 [SMILES: O=C(O)c1ccc(-n2cc(-c3cccc4c(=O)cc(N5CCCOCC5)[nH]c34)nn2)cc1] |
| 8-(1-(3-hydroxyphenyl)-1H-1,2,3-triazol-4-yl)-2-(1,4-oxazepan-4-yl)quinolin-4(1H)-one | 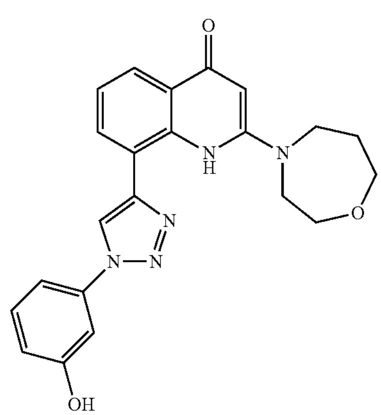 [SMILES: O=c1cc(N2CCCOCC2)[nH]c2c(-c3cn(-c4cccc(O)c4)nn3)cccc12] |

TABLE 1-continued

| Name | Structure |
|---|---|
| 8-(1-(3-hydroxy-4-methoxyphenyl)-1H-1,2,3-triazol-4-yl)-2-(1,4-oxazepan-4-yl)quinolin-4(1H)-one | 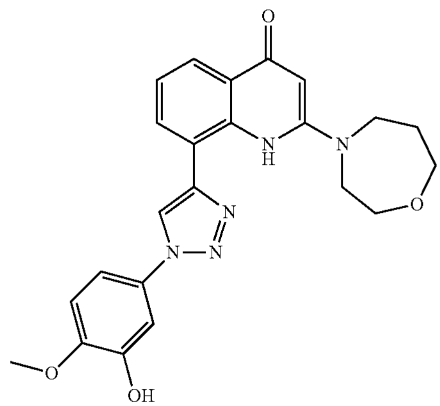 [SMILES: COc1ccc(-n2cc(-c3cccc4c(=O)cc(N5CCCOCC5)[nH]c34)nn2)cc1O] |
| 8-(1-(4-chlorophenyl)-1H-1,2,3-triazol-4-yl)-2-(1,4-oxazepan-4-yl)quinolin-4(1H)-one | 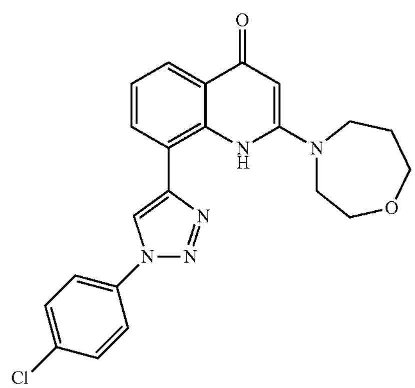 [SMILES: O=c1cc(N2CCCOCC2)[nH]c2c(-c3cn(-c4ccc(Cl)cc4)nn3)cccc12] |
| 8-(1-(4-methoxy-3-nitrophenyl)-1H-1,2,3-triazol-4-yl)-2-(1,4-oxazepan-4-yl)quinolin-4(1H)-one | 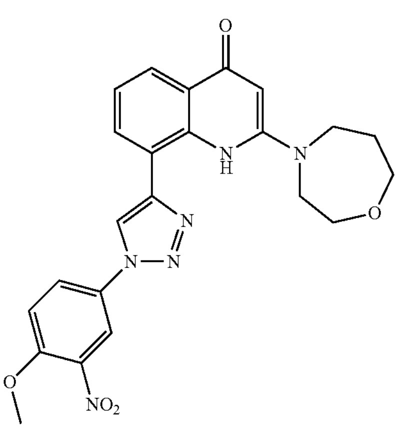 [SMILES: COc1ccc(-n2cc(-c3cccc4c(=O)cc(N5CCCOCC5)[nH]c34)nn2)cc1[N+](=O)[O-]] |

TABLE 1-continued

| Name | Structure |
|---|---|
| 8-(1-(3,5-dimethoxyphenyl)-1H-1,2,3-triazol-4-yl)-2-(1,4-oxazepan-4-yl)quinolin-4(1H)-one | 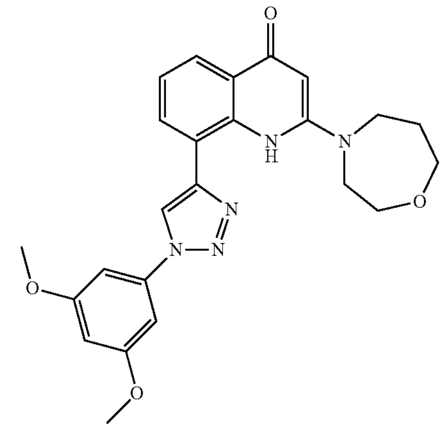 [SMILES: COc1cc(OC)cc(-n2cc(-c3cccc4c(=O)cc(N5CCCOCC5)[nH]c34)nn2)c1] |
| methyl 4-(4-(2-(1,4-oxazepan-4-yl)-4-oxo-1,4-dihydroquinolin-8-yl)-1H-1,2,3-triazol-1-yl)benzoate | 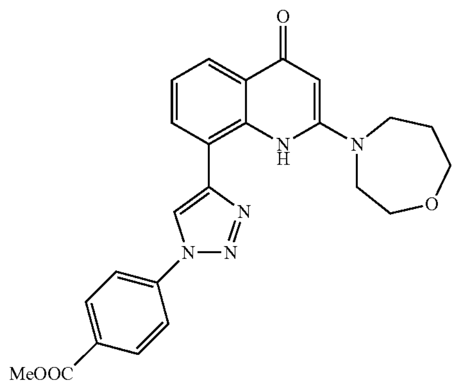 [SMILES: COC(=O)c1ccc(-n2cc(-c3cccc4c(=O)cc(N5CCCOCC5)[nH]c34)nn2)cc1] |
| 8-(1-(benzo[d][1,3]dioxol-5-yl)-1H-1,2,3-triazol-4-yl)-2-(1,4-oxazepan-4-yl)quinolin-4(1H)-one | 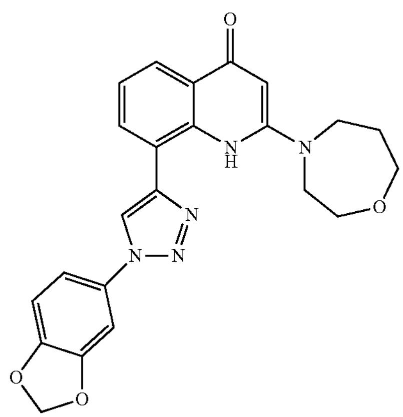 [SMILES: O=c1cc(N2CCCOCC2)[nH]c2c(-c3cn(-c4ccc5c(c4)OCO5)nn3)cccc12] |
| N-(3-(4-(2-(1,4-oxazepan-4-yl)-4-oxo-1,4-dihydroquinolin-8-yl)-1H-1,2,3-triazol-1-yl)-4-methoxyphenyl)acetamide | 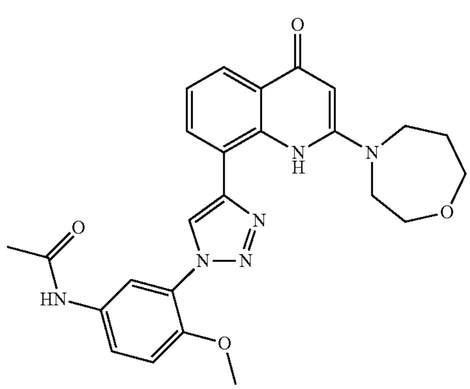 [SMILES: COc1ccc(NC(C)=O)cc1-n1cc(-c2cccc3c(=O)cc(N4CCCOCC4)[nH]c23)nn1] |

TABLE 1-continued

| Name | Structure |
|---|---|
| 8-(1-(4-hydroxy-2-methylphenyl)-1H-1,2,3-triazol-4-yl)-2-(1,4-oxazepan-4-yl)quinolin-4(1H)-one | 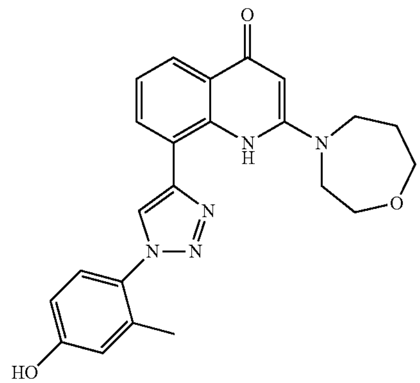 [SMILES: Cc1cc(O)ccc1-n1cc(-c2cccc3c(=O)cc(N4CCCOCC4)[nH]c23)nn1] |
| 2-(1,4-oxazepan-4-yl)-8-(1-(quinolin-3-yl)-1H-1,2,3-triazol-4-yl)quinolin-4(1H)-one | 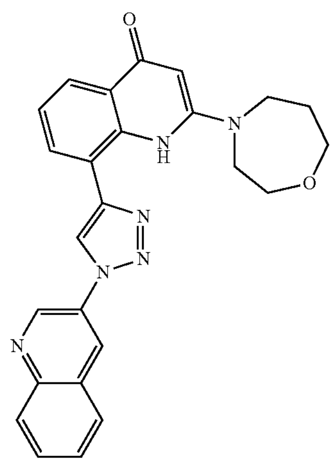 [SMILES: O=c1cc(N2CCCOCC2)[nH]c2c(-c3cn(-c4cnc5ccccc5c4)nn3)cccc12] |
| 2-(1,4-oxazepan-4-yl)-8-(1-(4-(trifluoromethoxy)phenyl)-1H-1,2,3-triazol-4-yl)quinolin-4(1H)-one | 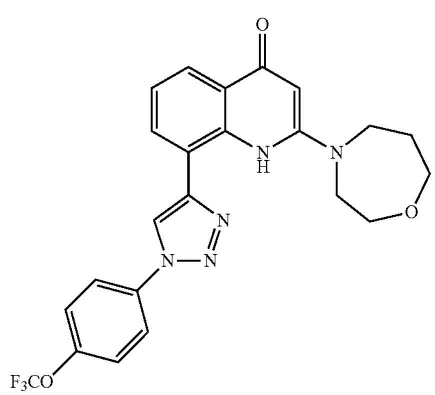 [SMILES: O=c1cc(N2CCCOCC2)[nH]c2c(-c3cn(-c4ccc(OC(F)(F)F)cc4)nn3)cccc12] |

TABLE 1-continued

| Name | Structure |
| --- | --- |
| 8-(1-(naphthalen-1-yl)-1H-1,2,3-triazol-4-yl)-2-(1,4-oxazepan-4-yl)quinolin-4(1H)-one | 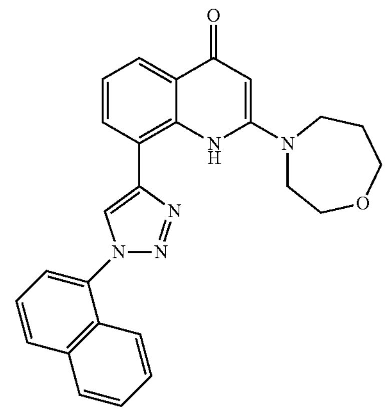 [SMILES: O=c1cc(N2CCCOCC2)[nH]c2c(-c3cn(-c4cccc5ccccc45)nn3)cccc12] |
| 8-(1-(naphthalen-2-yl)-1H-1,2,3-triazol-4-yl)-2-(1,4-oxazepan-4-yl)quinolin-4(1H)-one | 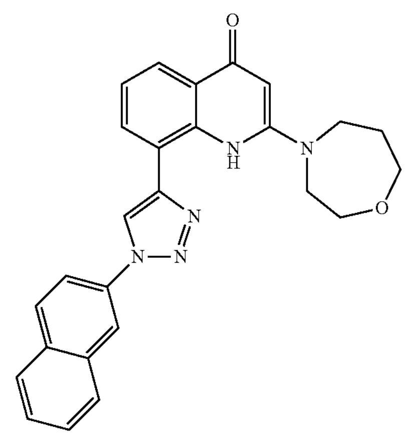 [SMILES: O=c1cc(N2CCCOCC2)[nH]c2c(-c3cn(-c4ccc5ccccc5c4)nn3)cccc12] |
| 8-(1-(4-aminophenyl)-1H-1,2,3-triazol-4-yl)-2-(1,4-oxazepan-4-yl)quinolin-4(1H)-one | 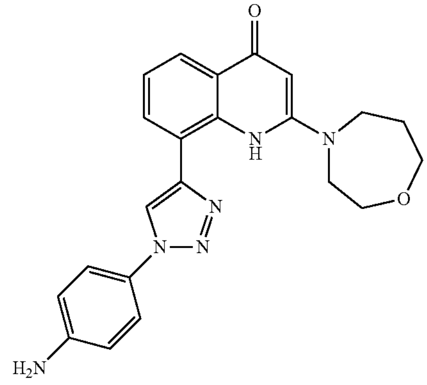 [SMILES: Nc1ccc(-n2cc(-c3cccc4c(=O)cc(N5CCCOCC5)[nH]c34)nn2)cc1] |

TABLE 1-continued

| Name | Structure |
|---|---|
| 8-(1-(3-methoxy-5-(trifluoromethoxy)phenyl)-1H-1,2,3-triazol-4-yl)-2-(1,4-oxazepan-4-yl)quinolin-4(1H)-one | 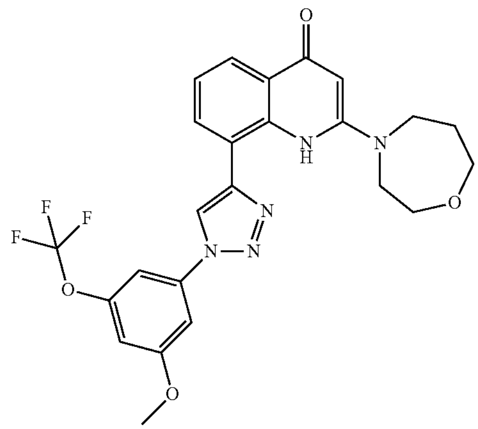 [SMILES: COc1cc(OC(F)(F)F)cc(-n2cc(-c3cccc4c(=O)cc(N5CCCOCC5)[nH]c34)nn2)c1] |
| 8-(1-(2-methoxyphenyl)-1H-1,2,3-triazol-4-yl)-2-(1,4-oxazepan-4-yl)quinolin-4(1H)-one | 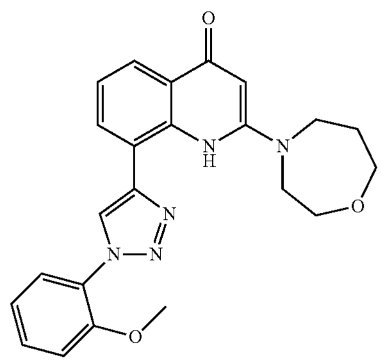 [SMILES: COc1ccccc1-n1cc(-c2cccc3c(=O)cc(N4CCCOCC4)[nH]c23)nn1] |
| 3-(4-(2-(1,4-oxazepan-4-yl)-4-oxo-1,4-dihydroquinolin-8-yl)-1H-1,2,3-triazol-1-yl)benzoic acid | 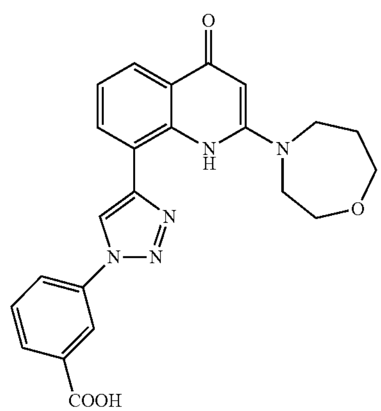 [SMILES: O=C(O)c1cccc(-n2cc(-c3cccc4c(=O)cc(N5CCCOCC5)[nH]c34)nn2)c1] |
| 8-(1-(3,4-dimethoxyphenyl)-1H-1,2,3-triazol-4-yl)-2-(1,4-oxazepan-4-yl)quinolin-4(1H)-one | 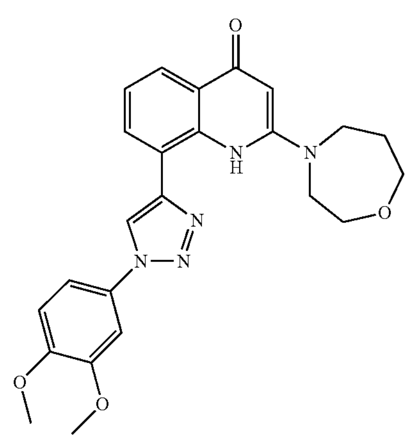 [SMILES: COc1ccc(-n2cc(-c3cccc4c(=O)cc(N5CCCOCC5)[nH]c34)nn2)cc1OC] |

TABLE 1-continued
| Name | Structure |
|---|---|
| 4-(4-(2-(1,4-oxazepan-4-yl)-4-oxo-1,4-dihydroquinolin-8-yl)-1H-1,2,3-triazol-1-yl)butanoic acid | 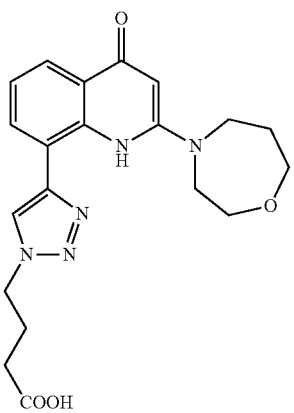 [SMILES: O=C(O)CCCn1cc(-c2cccc3c(=O)cc(N4CCCOCC4)[nH]c23)nn1] |
| methyl 3-(4-(2-(1,4-oxazepan-4-yl)-4-oxo-1,4-dihydroquinolin-8-yl)-1H-1,2,3-triazol-1-yl)benzoate | 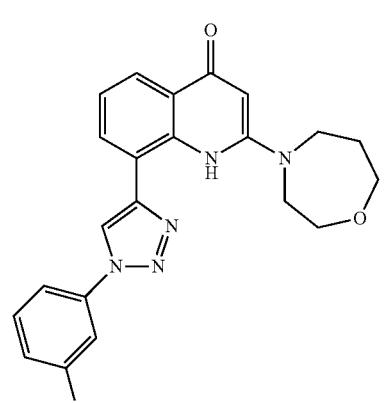 |
| 5-(4-(2-(1,4-oxazepan-4-yl)-4-oxo-1,4-dihydroquinolin-8-yl)-1H-1,2,3-triazol-1-yl)pentanoic acid | 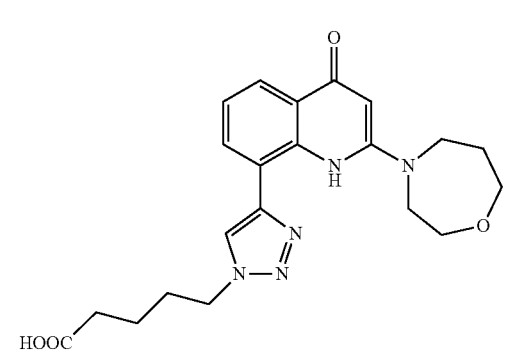 [SMILES: O=C(O)CCCCn1cc(-c2cccc3c(=O)cc(N4CCCOCC4)[nH]c23)nn1] |

TABLE 1-continued

| Name | Structure |
|---|---|
| 6-(4-(2-(1,4-oxazepan-4-yl)-4-oxo-1,4-dihydroquinolin-8-yl)-1H-1,2,3-triazol-1-yl)hexanoic acid | 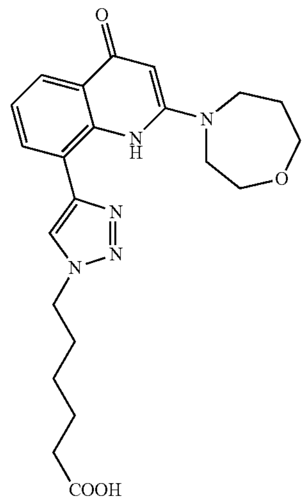 [SMILES: O=C(O)CCCCCn1cc(-c2cccc3c(=O)cc(N4CCCOCC4)[nH]c23)nn1] |
| N-(3-((4-(2-(1,4-oxazepan-4-yl)-4-oxo-1,4-dihydroquinolin-8-yl)-1H-1,2,3-triazol-1-yl)methyl)phenyl)-4-methylbenzenesulfonamide | 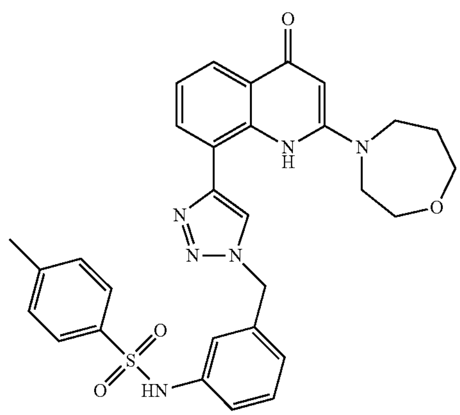 [SMILES: Cc1ccc(S(=O)(=O)Nc2cccc(Cn3cc(-c4cccc5c(=O)cc(N6CCCOCC6)[nH]c45)nn3)c2)cc1] |
| 4-(4-(2-(1,4-oxazepan-4-yl)-4-oxo-1,4-dihydroquinolin-8-yl)-1H-1,2,3-triazol-1-yl)benzenesulfonamide | 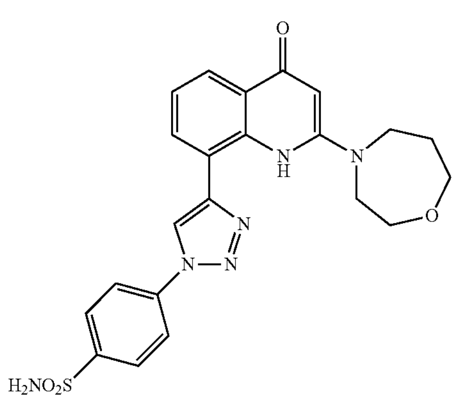 [SMILES: NS(=O)(=O)c1ccc(-n2cc(-c3cccc4c(=O)cc(N5CCCOCC5)[nH]c34)nn2)cc1] |

TABLE 1-continued
| Name | Structure |
|---|---|
| 4-(4-(2-(1,4-oxazepan-4-yl)-4-oxo-1,4-dihydroquinolin-8-yl)-1H-1,2,3-triazol-1-yl)-N-(phenylsulfonyl)benzamide | 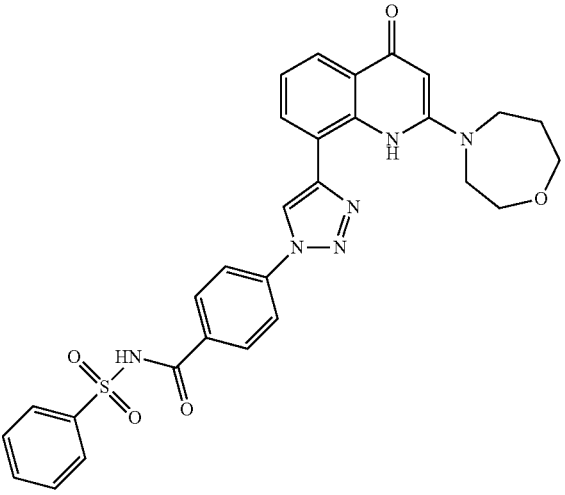 [SMILES: O=C(NS(=O)(=O)c1ccccc1)c1ccc(-n2cc(-c3cccc4c(=O)cc(N5CCCOCC5)[nH]c34)nn2)cc1] |
| 8-(1-(3-(1H-tetrazol-5-yl)benzyl)-1H-1,2,3-triazol-4-yl)-2-(1,4-oxazepan-4-yl)quinolin-4(1H)-one | 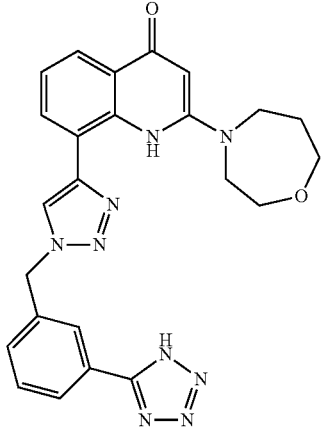 [SMILES: O=c1cc(N2CCCOCC2)[nH]c2c(-c3cn(Cc4cccc(-c5nnn[nH]5)c4)nn3)cccc12] |
| 8-(1-(4-(1H-tetrazol-5-yl)phenyl)-1H-1,2,3-triazol-4-yl)-2-(1,4-oxazepan-4-yl)quinolin-4(1H)-one | 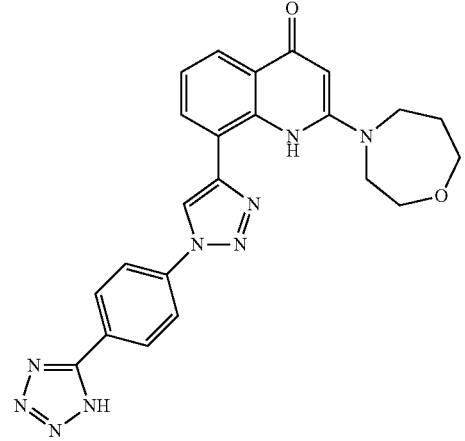 [SMILES: O=c1cc(N2CCCOCC2)[nH]c2c(-c3cn(-c4ccc(-c5nnn[nH]5)cc4)nn3)cccc12] |

Synthesis of Compounds of Formula (I)

The following scheme shows a method for preparing the compounds of the present description. For a more detailed description of the individual reaction steps, see the Examples hereinbelow.

Those skilled in the art will appreciate that other synthetic routes may be used to synthesize the compounds of the invention. Although specific starting materials and reagents are depicted in the scheme and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Compounds of formula (I) can be prepared as outlined in the Scheme a below.

Scheme a

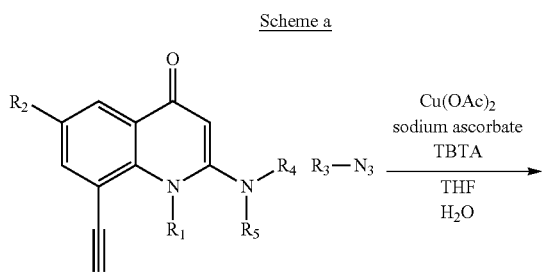

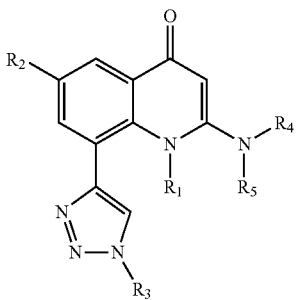

The 1,3-dipolar cycloaddition is catalyzed by the active copper(I) generated in situ by sodium ascorbate (Angew. Chem. Int. Ed. 2002, 41, 2596).

This catalytic activity is enhanced by TBTA, a powerful stabilizing ligand for copper(I), which protects it from oxidation and disproportionation (Org. Lett. 2004, 6, 2853-2855).

Azides are prepared applying synthetic methodology known in the art, while alkynes are prepared by adapting the procedure reported in F.-C. Ye et al. Synthesis, 1989, 317-320, as outlined in the Scheme b below.

Scheme b

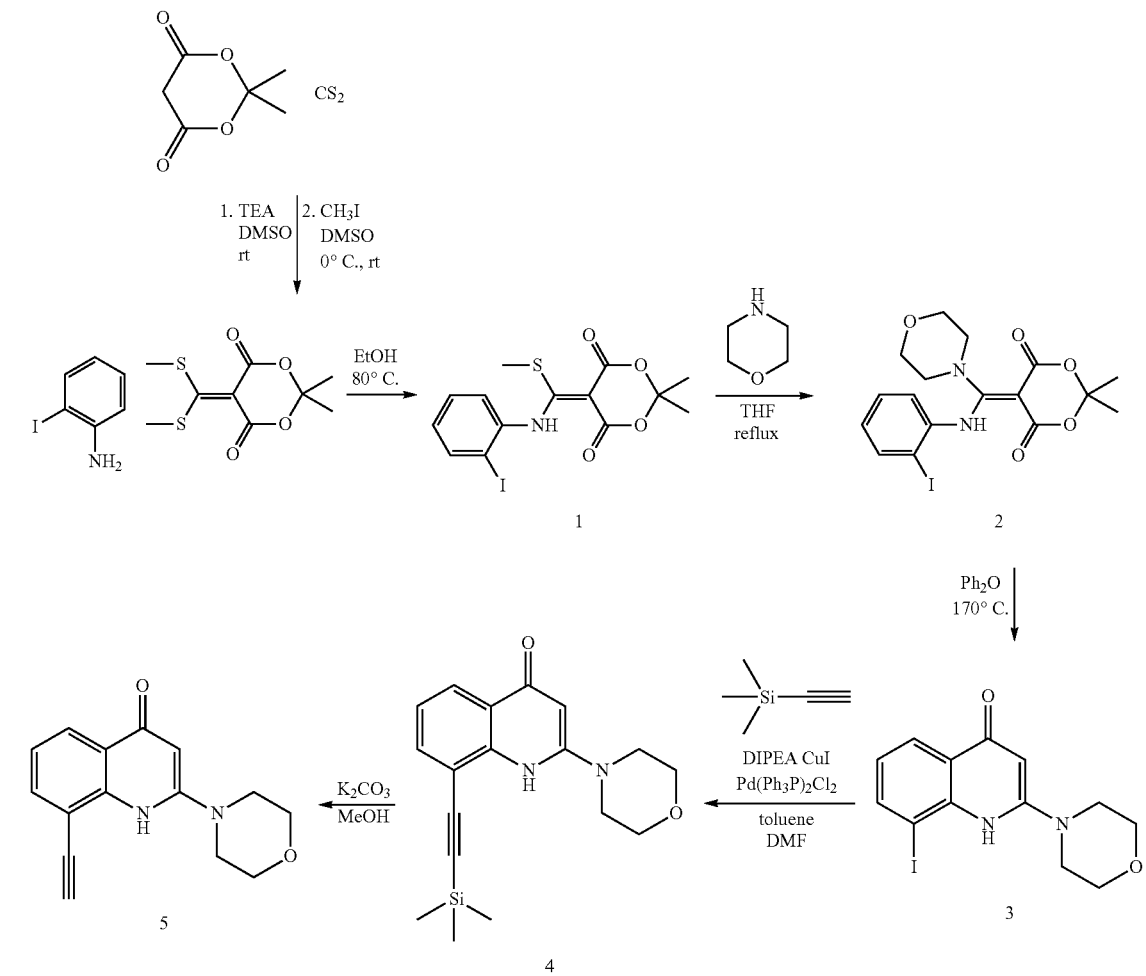

The synthesis of Intermediate 5 starts from 2-iodoaniline and Meldrum's acid derivative.

Substitution of Meldrum's acid derivative with 2-iodoaniline yields Intermediate 1, which after reaction with morpholine resulted in Intermediate 2.

The required quinolinone skeleton is constructed by refluxing Intermediate 3 in diphenyl ether for 15 minutes.

Subsequent Sonogashira reaction with trimethylsylilacetylene gives the protected alkyne 4 (Intermediate 4), which, after deprotection with potassium carbonate in methanol, yields the final alkyne (5).

The chemical reactions described in the Examples below may be readily adapted to prepare a number of other lipid kinase inhibitors of the invention, and alternative methods for preparing the compounds of this invention are deemed to be within the scope of this invention.

For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Example 1

Synthesis of 5-((2-iodophenylamino)(methylthio)methylene)-2,2-dimethyl-1,3-dioxane-4,6-dione (Intermediate 1)

A mixture of 5-(bis(methylthio)methylene)-2,2-dimethyl-1,3-dioxane-4,6-dione (453 mg, 1.83 mmol) and 2-iodoaniline (400 mg, 1.83 mmol) in ethanol (4 mL) was heated at 80° C. for 4 h. During the reaction, the product precipitates. Filtration yielded compound 1 (522 mg, 1.25 mmol, 68%) as a yellow solid.

Analytical Data:

$^1$H NMR (300 MHz; CDCl$_3$) δ 7.88 (d, J=7.4 Hz, 1H), 7.36 (m, 2H), 7.04 (t, J=7.4 Hz, 1H), 2.18 (s, 3H), 1.73 (s, 6H). $^{13}$C NMR (300 MHz; CDCl$_3$) δ 180.1, 141.8, 141.3, 131.1, 130.9, 128.9, 104.8, 98.2, 88.9, 59.8, 27.9, 20.3. MS: M+1 420

Example 2

Synthesis of 5-((2-iodophenylamino)(morpholino)methylene)-2,2-dimethyl-1,3-dioxane-4,6-dione (Intermediate 2)

A mixture of 5-((2-iodophenylamino)(methylthio) methylene)-2,2-dimethyl-1,3-dioxane-4,6-dione (500 mg, 1.23 mmol) and morpholine (214 µL, 2.46 mmol) in THF (5 mL) was heated at reflux overnight. The volatile is evaporated under reduced pressure. Diethyl ether is added and the solid is filtered and washed with ethyl acetate to give compound 2 as a white powder (429 mg, 0.94 mmol, 76%).

Analytical Data:

$^1$H NMR (300 MHz; CDCl$_3$) δ 9.57 (br s, 1H), 7.90 (d, J=7.7 Hz, 1H), 7.40 (t, J=7.7 Hz, 1H), 7.10 (d, J=7.7 Hz, 1H), 7.01 (t, J=7.7 Hz, 1H), 3.62 (t, J=4.4 Hz, 4H), 3.18 (t, J=4.4 Hz, 4H), 1.74 (s, 6H). $^{13}$C NMR (300 MHz; CDCl$_3$) δ 166.2, 165.9, 142.7, 141.9, 130.9, 130.1, 127.6, 103.9, 130.1, 127.6, 103.9, 97.6, 78.5, 66.7, 52.3, 28.0. MS: M−1 457

Example 3

Synthesis of 8-iodo-2-morpholinoquinolin-4(1H)-one (Intermediate 3)

5-((2-Iodophenylamino)(morpholino)methylene)-2,2-dimethyl-1,3-dioxane-4,6-dione (1 g, 2.18 mmol) was heated in diphenyl ether (10 mL) at reflux for 30 min. The crude brown oil, after purification by column chromatography using petroleum ether/ethyl acetate 5:5 and then ethyl acetate as eluent, yielded compound 3 (519 mg, 1.46 mmol, 67%) to give compound 3 as a white powder.

Analytical Data $^1$H NMR (300 MHz; CDCl$_3$) δ 8.18 (br s, 1H), 8.00 (d, J=6.6 Hz, 1H), 6.98 (br s, 1H), 5.77 (br s, 1H), 3.87 (br s, 4H), 3.83 (br s, 4H). $^{13}$C NMR (300 MHz; CDCl$_3$) δ 163.9, 160.7, 149.0, 141.6, 124.5, 124.4, 119.1, 102.5, 92.9, 68.0, 46.9. MS: M+1 357

Example 4

Synthesis of 2-morpholino-8-((trimethylsilyl)ethynyl) quinolin-4 (1H)-one (Intermediate 4)

To a solution of 8-iodo-2-morpholinoquinolin-4(1H)-one (100 mg, 0.280 mmol) in toluene (2 mL) and DMF (two drops) PdCl$_2$(PPh$_3$)$_2$ (6 mg, 0.00843 mmol), CuI (5 mg, 0.0252 mmol), DIPEA (48 µL, 0.280 mmol) and trimethylsilylacetilene (39 µL, 0.280 mmol) were added under nitrogen. The reaction is stirred at room temperature for 2 h. The reaction is diluted with water and extracted with EtOAc (×5). The collected organic layers are dried over sodium sulphate. The crude material is purified by column chromatography using ethyl acetate and then ethyl acetate/MeOH 95:5 as eluent, yielding compound 4 (66 mg, 0.202 mmol, 72%) as a yellow solid.

Analytical Data $^1$H NMR (300 MHz; CDCl$_3$) δ 8.12 (d, J 7.4, 1H), 7.59 (d, J 7.4 Hz, 1H), 7.11 (t, J=7.4 Hz, 1H), 5.86 (br s, 1H), 3.77 (t, J=4.7 Hz, 4H), 3.34 (t, J=4.7 Hz, 4H), 0.24 (s, 9H). MS: M+1 327

Example 5

Synthesis of 8-ethynyl-2-morpholinoquinolin-4(1H)-one (Alkyne 5)

To a solution of 2-morpholino-8-((trimethylsilyl) ethynyl) quinolin-4(1H)-one (1.87 g, 5.74 mmol) in methanol (20 mL) potassium carbonate (949 mg, 6.88 mmol) is added. The reaction is stirred at room temperature for 3 h. The volatile is removed under vacuo. The reaction is diluted with brine and extracted with CH$_2$Cl$_2$ (×4). The collected organic layers are dried over sodium sulphate. The crude material is purified by column chromatography using ethyl acetate and then ethyl acetate/MeOH 9:1 as eluent, yielding compound 5 (1.23 g, 4.83 mmol, 84%) as a yellow solid.

Analytical Data $^1$H NMR (300 MHz; CDCl$_3$) δ 8.19 (d, J=7.4 Hz, 1H), 7.66 (d, J=7.4 Hz, 1H), 7.17 (t, J=7.4 Hz, 1H), 5.90 (s, 1H), 3.79 (t, J=4.9 Hz, 4H), 3.61 (s, 1H), 3.37 (t, J=4.9 Hz, 4H). MS: M+1 255

Example 6

Synthesis of 8-(1-(2-hydroxyphenyl)-1H-1,2,3-triazol-4-yl)-2-morpholinoquinolin-4(1H)-one (identified as TP 714, CL31c)

To a solution of Cu(OAc)$_2$ (2 mg, 0.00985 mmol) in THF (0.5 mL) TBTA (6 mg, 0.00985 mmol) is added and the resulting mixture is stirred at room temperature for 30 min. A solution of the azide (the compound R$_3$—N$_3$ in scheme a) (27 mg, 0.197 mmol) in THF (0.5 mL), a solution of the alkyne 5 (50 mg, 0.197 mmol) in THF (0.5 mL) and a solution of sodium ascorbate (4 mg, 0.0197 mmol) in the minimum amount of water are added. The reaction is stirred at room temperature overnight. The product precipitates. It is filtered and washed with diethyl ether to give a brown solid (58 mg, 0.149 mmol, 76%).
Analytical Data
$^1$H NMR (300 MHz; DMSO-d6) δ 9.38 (s, 1H), 8.43 (s, 1H), 7.94 (d, J=7.7 Hz, 1H), 7.78 (d, J=7.1 Hz, 1H), 7.28 (m, 2H), 7.15 (d, J=8.2 Hz, 1H), 7.00 (t, J=7.7 Hz, 1H), 6.55 (br s, 1H), 3.75 (br s, 4H), 3.54 (br s, 4H) MS: M+1 390

Example 7

Synthesis of 2-morpholino-8-(1-phenyl-1h-1,2,3-triazol-4-yl)quinolin-4(1H)-one (identified as CL1)

The title compound was synthesized following the procedure described for Example 6. The product was obtained as a yellow solid (90%).
Analytical Data
$^1$H NMR (300 MHz; DMSO-d6) δ 9.30 (br s, 1H), 8.39 (br s, 1H), 7.93 (m, 3H), 7.63 (t, J=7.7 Hz, 2H), 7.49 (m, 1H), 7.30 (t, J=7.7 Hz, 1H), 6.51 (br s, 1H), 3.76 (br s, 4H), 3.56 (br s, 4H). MS: M+1 374

Example 8

Synthesis of 8-(1-benzyl-1H-1,2,3-triazol-4-yl)-2-morpholinoquinolin-4(1H)-one (identified as CL5)

The title compound was synthesized following the procedure described for Example 69. The product was obtained as a light yellow solid (84%).
Analytical Data
$^1$H NMR (300 MHz; CD3OD) δ 8.57 (s, 1H), 8.03 (d, J=7.7 Hz, 1H), 7.83 (d, J=7.7 Hz, 1H), 7.40 (m, 5H), 7.24 (t, J 7.7 Hz, 1H), 5.81 (s, 1H), 5.68 (s, 2H), 3.87 (br t, 4H), 3.51 (br t, 1H). MS: M+1 388

Example 9

Synthesis of 8-(1-(3-methoxyphenyl)-1H-1,2,3-triazol-4-yl)-2-morpholinoquinolin-4 (1H)-one (identified as CL6)

The title compound was synthesized following the procedure described for Example 9. The product was obtained as a yellow solid (57%).
Analytical Data
$^1$H NMR (300 MHz; CD$_3$OD) δ 9.03 (s, 1H), 8.08 (d, J 7.7 Hz, 1H), 7.92 (d, J=7.4 Hz, 1H), 7.44 (m, 3H), 7.26 (t, J=7.9 Hz, 1H), 7.04 (m, 1H), 5.79 (br s, 1H), 3.89 (s, 3H), 3.84 (t, J=4.9 Hz, 4H), 3.49 (t, J=4.9 Hz, 4H). MS: M+1 404

Example 10

Synthesis of 2-morpholino-8-(1-(pyridin-4-yl)-1H-1,2,3-triazol-4-yl)quinolin-4(1H)-one (identified as CL8)

The title compound was synthesized following the procedure described for Example 9. The product was obtained as a yellow solid (50%).
Analytical Data
$^1$H NMR (300 MHz; DMSO-d6) δ 7.94 (d, J=7.4 Hz, 1H), 7.88 (s, 1H), 7.82 (d, J=7.7 Hz, 1H), 7.45 (t, J=7.4 Hz, 1H), 7.29 (m, 3H), 6.97 (s, 1H), 5.70 (s, 1H), 3.79 (br s, 4H), 3.19 (br s, 4H). MS: M−1 373

Example 11

Synthesis of 8-(1-(4-(benzyloxy)phenyl)-1H-1,2,3-triazol-4-yl)-2-morpholinoquinolin-4(1H)-one (identified as CL9)

The title compound was synthesized following the procedure described for Example 9. The product was obtained as a yellow solid (55%).
Analytical Data
$^1$H NMR (300 MHz; DMSO-d6) δ 8.40 (br s, 1H), 7.95 (d, J=7.9 Hz, 1H), 7.81 (m, 2H), 7.48-7.24 (m, 9H), 6.51 (s, 1H), 5.19 (s, 2H), 3.76 (m, 4H), 3.57 (m, 4H). MS: M+1 480

Example 12

Synthesis of 2-(4-(4-(2-morpholino-4-oxo-1,4-dihydroquinolin-8-yl)-1H-1,2,3-triazol-1-yl)phenyl)acetonitrile (identified as CL12)

The title compound was synthesized following the procedure described for Example 9. The product was obtained as a yellow solid (74%).
Analytical Data
$^1$H NMR (300 MHz; DMSO-d6) δ 8.39 (br s, 1H), 7.96 (m, 4H), 7.60 (d, J=8.5 Hz, 2H), 7.30 (t, J=7.4 Hz, 1H), 6.55 (br s, 1H), 4.14 (s, 2H), 3.77 (br s, 4H), 3.55 (br s, 4H). MS: M+1 413

Example 13

Synthesis of methyl 4-((4-(2-morpholino-4-oxo-1,4-dihydroquinolin-8-yl)-1H-1,2,3-triazol-1-yl)methyl)benzoate (identified as CL27a)

The title compound was synthesized following the procedure described for Example 9. The product was obtained as a grey solid (90%).
Analytical Data
$^1$H NMR (300 MHz; DMSO-d6) δ 8.72 (br s, 1H), 8.36 (br s, 1H), 7.99 (d, J 8.2, 2H), 7.91 (br s, 1H), 7.52 (d, J=8.2 Hz, 2H), 7.26 (t, J=7.7 Hz, 1H), 6.47 (br s, 1H), 5.81 (s, 2H), 3.95 (s, 3H), 3.66 (m, 4H), 3.56 (m, 4H). MS: M+1 446

Example 14

Synthesis of 2-((4-(2-morpholino-4-oxo-1,4-dihydroquinolin-8-yl)-1H-1,2,3-triazol-1-yl)methyl)benzonitrile (identified as CL27b)

The title compound was synthesized following the procedure described for Example 9. The product was obtained as a yellow solid (84%).

Analytical Data

¹H NMR (300 MHz; DMSO-d6) δ 8.74 (s, 1H), 8.38 (d, J=7.1 Hz, 1H), 7.94 (t, J=6.6 Hz, 1H), 7.79 (t, J=7.1 Hz, 1H), 7.62 (m, 2H), 7.29 (m, 2H), 6.49 (br s, 1H), 5.89 (s, 2H), 3.65 (m, 4H), 3.50 (m, 4H). MS: M+1 413

Example 15

Synthesis of methyl 3-((4-(2-morpholino-4-oxo-1,4-dihydroquinolin-8-yl)-1H-1,2,3-triazol-1-yl)methyl)benzoate (identified as CL27c)

The title compound was synthesized following the procedure described for Example 9. The product was obtained as a white solid (95%).

Analytical Data

¹H NMR (300 MHz; DMSO-d6) δ 8.72 (s, 1H), 8.37 (d, J=7.7 Hz, 1H), 8.02 (s, 1H), 7.96 (m, 2H), 7.71 (d, J=7.4 Hz, 1H), 7.59 (t, J=7.7 Hz, 1H), 7.28 (t, J=7.9 Hz, 1H), 6.47 (s, 1H), 5.82 (s, 2H), 3.85 (s, 3H), 3.68 (m, 4H), 3.48 (m, 4H). MS: M+1 446

Example 16

Synthesis of 8-(1-(2-(1H-indol-3-yl)ethyl)-1H-1,2,3-triazol-4-yl)-2-morpholinoquinolin-4(1H)-one (identified as CL27d)

The title compound was synthesized following the procedure described for Example 9. The product was obtained as a yellow oil (90%).

Analytical Data

¹H NMR (300 MHz; DMSO-d6) δ 8.61 (s, 1H), 8.37 (d, J=6.9 Hz, 1H), 7.93 (m, 2H), 7.57 (d, J=7.1 Hz, 1H), 7.30 (m, 2H), 7.02 (m, 2H), 6.48 (s, 1H), 4.77 (t, 7.1 Hz, 2H), 3.82 (m, 4H), 3.65 (m, 4H), 3.58 (t, 7.1 Hz, 2H). MS: M+1 441

Example 17

Synthesis of 3-((4-(2-morpholino-4-oxo-1,4-dihydroquinolin-8-yl)-1H-1,2,3-triazol-1-yl)methyl)benzoic acid (identified as CL27e)

The title compound was synthesized following the procedure described for Example 9. The product was obtained as a yellow solid (70%).

Analytical Data

¹H NMR (300 MHz; DMSO-d6) δ 8.08 (s, 1H), 8.00 (d, J=7.7 Hz, 1H), 7.93 (d, J=3.3 Hz, 1H), 7.88 (d, J=7.1 Hz, 1H), 7.51 (t, J=7.7 Hz, 1H), 7.31 (m, 2H), 7.02 (d, J=3.3 Hz, 1H), 6.50 (br s, 1H), 5.75 (s, 2H), 3.83 (m, 4H), 3.25 (m, 4H). MS: M+1 432

Example 18

Synthesis of 8-(1-(4-methoxyphenyl)-1H-1,2,3-triazol-4-yl)-2-morpholinoquinolin-4 (1H)-one (identified as CL27f)

The title compound was synthesized following the procedure described for Example 9. The product was obtained as a light yellow solid (55%).

Analytical Data

¹H NMR (300 MHz; DMSO-d6) δ 9.21 (br s, 1H), 8.39 (br s, 1H), 8.00 (d, J=7.9 Hz, 1H), 7.85 (d, J=7.7 Hz, 2H), 7.33 (t, J=7.1 Hz, 1H), 7.20 (d, J=7.1 Hz, 2H), 3.86 (s, 3H), 3.79 (br s, 4H), 3.57 (br s, 4H). MS: M+1 404

Example 19

Synthesis of 4-(4-(2-morpholino-4-oxo-1,4-dihydroquinolin-8-yl)-1H-1,2,3-triazol-1-yl)benzoic acid (identified as CL29a, CL38)

The title compound was synthesized following the procedure described for Example 9. The product was obtained as a yellow solid (66%).

Analytical Data

¹H NMR (300 MHz; DMSO-d6) δ 9.39 (br s, 1H), 8.42 (d, J=6.9 Hz, 2H), 8.09 (m, 2H), 7.97 (d, J=6.9 Hz, 2H), 7.33 (t, J=8.2 Hz, 1H), 6.54 (s, 1H), 3.78 (br s, 4H), 3.59 (br s, 4H). MS: M+1 418

Example 20

Synthesis of 8-(1-(3-hydroxyphenyl)-1H-1,2,3-triazol-4-yl)-2-morpholinoquinolin-4 (1H)-one (identified as CL29b)

The title compound was synthesized following the procedure described for Example 9. The product was obtained as a yellow solid (90%).

Analytical Data

¹H NMR (300 MHz; DMSO-d6) δ 9.25 (br s, 1H), 8.37 (br s, 1H), 7.95 (d, J=6.8 Hz, 1H), 7.39 (t, J=8.2 Hz, 1H), 7.29 (m, 3H), 6.86 (d, J=7.9 Hz, 1H), 6.49 (br s, 1H), 3.75 (m, 4H), 3.54 (m, 4H). MS: M+1 389

Example 21

Synthesis of methyl 3-((4-(2-morpholino-4-oxo-1,4-dihydroquinolin-8-yl)-1H-1,2,3-triazol-1-yl)methyl)benzoate (identified as CL29c)

The title compound was synthesized following the procedure described for Example 9. The product was obtained as a yellow solid (40%).

Analytical Data

¹H NMR (300 MHz; DMSO-d6) δ 9.18 (br s, 1H), 8.47 (br s, 1H), 8.00 (br s, 1H), 7.33 (m, 3H), 7.17 (d, J=8.8 Hz, 1H), 6.51 (br s, 1H), 3.86 (s, 3H), 3.75 (m, 4H), 3.54 (m, 4H). MS: M+1 420

Example 22

Synthesis of 8-(1-(2-(1H-indol-3-yl)ethyl)-1H-1,2,3-triazol-4-yl)-2-morpholinoquinolin-4(1H)-one (identified as CL29d)

The title compound was synthesized following the procedure described for Example 9. The product was obtained as a light grey solid (50%).

Analytical Data

¹H NMR (300 MHz; DMSO-d6) δ 8.48 (br s, 1H), 7.98 (m, 4H), 7.73 (m, 2H), 7.34 (t, J=7.7 Hz, 1H), 6.50 (br s, 1H), 3.80 (m, 4H), 3.59 (m, 4H). MS: M+1 408

Example 23

Synthesis of 3-((4-(2-morpholino-4-oxo-1,4-dihydroquinolin-8-yl)-1H-1,2,3-triazol-1-yl)methyl)benzoic acid (identified as CL29e)

The title compound was synthesized following the procedure described for Example 9. The product was obtained as a yellow solid (50%).

Analytical Data $^1$H NMR (300 MHz; DMSO-d6) δ 9.40 (s, 1H), 8.47 (s, 1H), 8.25 (d, J=9.0 Hz, 1H), 8.00 (d, J=9.0 Hz, 1H), 7.65 (m, 2H), 7.34 (t, J=7.4 Hz, 1H), 6.53 (br s, 1H), 4.03 (s, 3H), 3.80 (m, 4H), 3.60 (m, 4H). MS: M+1 448

Example 24

Synthesis of 8-(1-(3,5-dimethoxyphenyl)-1H-1,2,3-triazol-4-yl)-2-morpholinoquinolin-4(1H)-one (identified as CL30a)

The title compound was synthesized following the procedure described for Example 9. The product was obtained as a yellow solid (84%).

Analytical Data:

$^1$H NMR (300 MHz; DMSO-d6) δ 9.46 (s, 1H), 8.48 (s, 1H), 8.07 (m, 1H), 7.45 (m, 1H), 7.18 (m, 3H), 6.72 (s, 1H), 3.86 (s, 6H) 3.78 (m, 4H), 3.65 (m, 4H). MS: M+1 434

Example 25

Synthesis of methyl 4-(4-(2-morpholino-4-oxo-1,4-dihydroquinolin-8-yl)-1H-1,2,3-triazol-1-yl)benzoate (identified as CL30b)

The title compound was synthesized following the procedure described for Example 9. The product was obtained as a yellow solid (90%).

Analytical Data:

$^1$H NMR (300 MHz; DMSO-d6) δ 9.40 (s, 1H), 8.42 (d, J=7.7 Hz, 1H), 8.24-8.12 (m, 5H), 7.35 (t, J=7.7 Hz, 1H), 6.48 (br s, 1H), 3.94 (s, 3H), 3.83 (m, 4H), 3.63 (m, 4H). MS: M+1 432

Example 26

Synthesis of 8-(1-(benzo[d][1,3]dioxol-5-yl)-1H-1,2,3-triazol-4-yl)-2-morpholinoquinolin-4(1H)-one (identified as CL31a)

The title compound was synthesized following the procedure described for Example 9. The product was obtained as a yellow solid (91%).

Analytical Data:

$^1$H NMR (300 MHz; DMSO-d6) δ 9.23 (s, 1H), 8.42 (br s, 1H), 8.00 (d, J=7.7 Hz, 1H), 7.54 (s, 1H), 7.33 (t, J=7.7 Hz, 1H), 7.16 (m, 2H), 6.58 (br s, 1H), 6.19 (s, 2H), 3.78 (br s, 4H), 3.58 (br s, 4H). MS: M+1 418

Example 27

Synthesis of N-(4-methoxy-3-(4-(2-morpholino-4-oxo-1,4-dihydroquinolin-8-yl)-1H-1,2,3-triazol-1-yl) phenyl) acetamide (identified as CL31b)

The title compound was synthesized following the procedure described for Example 9. The product was obtained as a yellow solid (78%).

Analytical Data:

$^1$H NMR (300 MHz; DMSO-d6) δ 10.1 (s, 1H), 9.25 (s, 1H), 8.53 (d, J=6.8 Hz, 1H), 8.13 (d, J=2.5 Hz, 1H), 8.00 (d, J=6.8 Hz, 1H), 7.67 (dd, J 8.8, 2.5 Hz, 1H), 7.31 (m, 2H), 6.55 (br s, 1H), 3.88 (s, 3H), 3.79 (m, 4H), 3.58 (m, 4H), 2.06 (s, 3H). MS: M+1 461

Example 28

Synthesis of 8-(1-(4-hydroxy-2-methylphenyl)-1H-1,2,3-triazol-4-yl)-2-morpholinoquinolin-4(1H)-one (identified as CL31d)

The title compound was synthesized following the procedure described for Example 9. The product was obtained as a brown solid (31%).

Analytical Data:

$^1$H NMR (300 MHz; DMSO-d6) δ 8.86 (br s, 1H), 8.43 (br s, 1H), 7.99 (br s, 1H), 7.32 (m, 2H), 6.81 (m, 2H), 6.70 (br s, 1H), 3.73 (m, 4H), 3.52 (m, 4H), 2.14 (s, 3H). MS: M+1 404

Example 29

Synthesis of 2-morpholino-8-(1-(quinolin-3-yl)-1H-1,2,3-triazol-4-yl)quinolin-4(1H)-one (identified as CL32a)

The title compound was synthesized following the procedure described for Example 9. The product was obtained as a yellow solid (93%).

Analytical Data:

$^1$H NMR (300 MHz; DMSO-d6) δ 9.53 (s, 1H), 8.97 (m, 2H), 8.40 (s, 1H), 8.18 (m, 2H), 7.97 (s, 1H), 7.90 (t, J=7.1 Hz, 1H), 7.77 (t, J=7.4 Hz, 1H), 7.36 (t, J=7.1 Hz, 1H), 6.52 (br s, 1H), 3.81 (m, 4H), 3.64 (m, 4H). MS: M+1 425

Example 30

Synthesis of 2-morpholino-8-(1-(4-(trifluoromethoxy)phenyl)-1H-1,2,3-triazol-4-yl)quinolin-4(1H)-one (identified as CL32b)

The title compound was synthesized following the procedure described for Example 9. The product was obtained as a yellow solid (69%).

Analytical Data:

$^1$H NMR (300 MHz; DMSO-d6) δ 9.38 (s, 1H), 8.45 (br s, 1H), 8.03 (m, 4H), 7.69 (d, J=7.7 Hz, 1H), 7.35 (t, J=7.2 Hz, 1H), 6.55 (br s, 1H), 3.81 (m, 4H), 3.61 (m, 4H). MS: M+1 458

Example 31

Synthesis of 2-morpholino-8-(1-(naphthalen-1-yl)-1H-1,2,3-triazol-4-yl)quinolin-4(1H)-one (identified as CL32c)

The title compound was synthesized following the procedure described for Example 9. The product was obtained as a yellow solid (90%).

Analytical Data:

$^1$H NMR (300 MHz; DMSO-d6) δ 9.21 (s, 1H), 8.50 (d, J=6.0 Hz, 1H), 8.20 (m, 3H), 8.01 (d, J=7.9 Hz, 1H), 7.85 (d, J=7.4 Hz, 1H), 7.74 (m, 3H), 7.37 (t, J=7.7 Hz, 1H), 6.54 (s, 1H), 3.83 (m, 4H), 3.64 (m, 4H). MS: M+1 424

Example 32

Synthesis of 2-morpholino-8-(1-(naphthalen-2-yl)-1H-1,2,3-triazol-4-yl)quinolin-4(1H)-one (identified as CL33a)

The title compound was synthesized following the procedure described for Example 9. The product was obtained as a yellow solid (68%).
Analytical Data:
$^1$H NMR (300 MHz; DMSO-d6) δ 9.56 (br s, 1H), 8.54 (m, 2H), 8.27-8.10 (m, 5H), 770 (m, 2H), 7.42 (br s, 1H), 6.61 (br s, 1H), 3.80 (m, 4H), 3.65 (m, 4H). MS: M+1 424

Example 33

Synthesis of 8-(1-(4-aminophenyl)-1H-1,2,3-triazol-4-yl)-2-morpholinoquinolin-4(1H)-one (identified as CL33b)

The title compound was synthesized following the procedure described for Example 9. The product was obtained as a black solid (65%).
Analytical Data:
$^1$H NMR (300 MHz; DMSO-$d_6$) δ 9.09 (s, 1H), 8.42 (br s, 2H), 7.95 (m, 2H), 7.50 (d, J=8.5 Hz, 2H), 7.32 (t, J=7.7 Hz, 1H), 6.75 (d, J=8.5 Hz, 2H), 6.62 (br s, 1H), 3.82 (m, 4H), 3.58 (m, 4H). MS: M+1 389

Example 34

Synthesis of 8-(1-(3-methoxy-5-(trifluoromethoxy)phenyl)-1H-1,2,3-triazol-4-yl)-2-morpholinoquinolin-4 (1H)-one (identified as CL35a)

The title compound was synthesized following the procedure described for Example 9. The product was obtained as a light yellow solid (90%).
Analytical Data:
$^1$H NMR (300 MHz; DMSO-$d_6$) δ 9.52 (s, 1H), 8.43 (d, J=6.9 Hz, 1H), 8.00 (d, J=7.7 Hz, 1H), 7.84 (s, 2H), 7.41 (s, 1H), 7.35 (t, J=7.7 Hz, 1H), 6.55 (br s, 1H), 3.98 (s, 3H), 3.77 (m, 4H), 3.62 (m, 4H). MS: M+1 472

Example 35

Synthesis of 8-(1-(2-methoxyphenyl)-1H-1,2,3-triazol-4-yl)-2-morpholinoquinolin-4(1H)-one (identified as CL35b)

The title compound was synthesized following the procedure described for Example 9. The product was obtained as a yellow amorphous solid (90%).
Analytical Data:
$^1$H NMR (300 MHz; DMSO-$d_6$) δ 9.23 (s, 1H), 8.52 (d, J=7.7 Hz, 1H), 7.99 (t, J=7.4 Hz, 1H), 7.77 (d, J=7.7 Hz, 1H), 7.53 (t, J=7.4 Hz, 1H), 7.35 (m, 2H), 7.20 (t, 7.7 Hz, 1H), 6.54 (br s, 1H), 3.91 (s, 3H), 3.78 (m, 4H), 3.58 (m, 4H). MS: M+1 404

Example 36

Synthesis of 8-(1-(3,4-dimethoxyphenyl)-1H-1,2,3-triazol-4-yl)-2-morpholinoquinolin-4(1H)-one (identified as CL35d)

The title compound was synthesized following the procedure described for Example 9. The product was obtained as a grey amorphous solid (77%).
Analytical Data:
$^1$H NMR (300 MHz; DMSO-$d_6$) δ 9.29 (s, 1H), 8.43 (d, J=6.6 Hz, 1H), 7.98 (d, J=7.7 Hz, 1H), 7.51 (s, 1H), 7.43 (d, 8.5 Hz, 1H), 7.33 (t, J=7.7 Hz, 1H), 7.20 (d, J=8.5 Hz, 1H), 6.55 (s, 1H), 3.90 (s, 3H), 3.85 (s, 3H), 3.78 (m, 4H), 3.62 (m, 4H). MS: M+1 434

Example 37

Synthesis of 4-(4-(2-morpholino-4-oxo-1,4-dihydroquinolin-8-yl)-1H-1,2,3-triazol-1-yl)butanoic acid (identified as CL55a)

The title compound was synthesized following the procedure described for Example 9. The product was obtained as a yellow solid (47%).
Analytical Data:
$^1$H NMR (300 MHz; DMSO-$d_6$) δ 8.81 (s, 1H), 8.39 (d, J=7.7 Hz, 1H), 7.98 (d, J=7.7 Hz, 1H), 7.35 (d, 7.7 Hz, 1H), 6.60 (br s, 1H), 4.56 (t, J=7.1 Hz, 2H), 3.83 (m, 4H), 3.59 (m, 4H), 2.34 (t, J=7.1 Hz, 2H), 2.15 (quint, J=7.1 Hz, 2H). MS: M+1 384

Example 38

Synthesis of 3-(4-(2-morpholino-4-oxo-1,4-dihydroquinolin-8-yl)-1H-1,2,3-triazol-1-yl)benzoic acid (identified as CL55b)

The title compound was synthesized following the procedure described for Example 9. The product was obtained as a yellow solid (89%).
Analytical Data:
$^1$H NMR (300 MHz; DMSO-$d_6$) δ 9.42 (s, 1H), 8.40 (m, 2H), 8.16 (d, J=8.2 Hz, 1H), 8.06 (m, 2H), 7.76 (t, J=7.7 Hz, 1H), 7.34 (t, J=7.7 Hz, 1H), 6.58 (br s, 1H), 3.85 (m, 4H), 3.63 (m, 4H). MS: M+1 418

Example 39

Synthesis of methyl 3-(4-(2-morpholino-4-oxo-1,4-dihydroquinolin-8-yl)-1H-1,2,3-triazol-1-yl)benzoate (identified as CL55c)

The title compound was synthesized following the procedure described for Example 9. The product was obtained as a yellow solid (62%).
Analytical Data:
$^1$H NMR (300 MHz; DMSO-$d_6$) δ 8.40 (m, 2H), 8.27 (d, J=7.1 Hz, 1H), 8.04 (m, 3H), 7.82 (t, J=7.9 Hz, 1H), 7.35 (t, J=7.4 Hz, 1H), 6.53 (br s, 1H), 4.01 (s, 3H), 3.83 (m, 4H), 3.61 (m, 4H). MS: M+1 432

Example 40

Synthesis of 6-(4-(2-morpholino-4-oxo-1,4-dihydroquinolin-8-yl)-1H-1,2,3-triazol-1-yl)hexanoic acid (identified as CL58a)

The title compound was synthesized following the procedure described for Example 9. The product was obtained as a yellow solid (40%).
Analytical Data:
$^1$H NMR (300 MHz; DMSO-$d_6$) δ 8.77 (s, 1H), 8.29 (d, J=7.1 Hz, 1H), 7.95 (d, J=7.1 Hz, 1H), 7.32 (t, J=7.1 Hz, 1H), 6.58 (br s, 1H), 4.49 (t, J=6.9 Hz, 1H), 3.79 (m, 4H), 3.53 (m, 4H), 2.21 (t, J=6.9 Hz, 2H), 1.89 (m, 2H), 1.55 (m, 2H), 1.31 (m, 2H). MS: M+1 412

Example 41

Synthesis of 5-(4-(2-morpholino-4-oxo-1,4-dihydroquinolin-8-yl)-1H-1,2,3-triazol-1-yl)pentanoic acid (identified as CL 64a)

The title compound was synthesized following the procedure described for Example 9. The product was obtained as a yellow solid (40%).
Analytical Data:
$^1$H NMR (300 MHz; DMSO-$d_6$) δ 8.79 (br s, 1H), 8.29 (br s, 1H), 7.95 (d, J=7.7 Hz), 7.29 (t, J=7.7 Hz, 1H), 6.53 (br s, 1H), 4.50 (t, J=7.4 Hz, 1H), 3.78 (m, 4H), 3.61 (m, 4H), 2.27 (t, J=7.4 Hz, 2H), 1.89 (quint, J=7.4 Hz, 2H), 1.52 (quint, J=7.4 Hz, 2H). MS: M+1 398

Example 42

Synthesis of 8-(1-(2-(hydroxymethyl)phenyl)-1H-1,2,3-triazol-4-yl)-2-morpholinoquinolin-4(1H)-one (identified as CL 64b)

The title compound was synthesized following the procedure described for Example 9. The product was obtained as a yellow solid (40%).
Analytical Data:
$^1$H NMR (300 MHz; DMSO-$d_6$) δ 9.16 (d, J=7.4 Hz, 1H), 8.47 (br s, 1H), 7.95 (m, 2H), 7.55 (m, 2H), 7.33 (m, 1H), 7.03 (t, J=7.4 Hz, 1H), 6.60 (br s, 1H), 4.46 (s, 2H), 3.74 (m, 4H), 3.60 (m, 4H). MS: M+1 404

Example 43

Synthesis of 4-(4-(2-morpholino-4-oxo-1,4-dihydroquinolin-8-yl)-1H-1,2,3-triazol-1-yl)benzenesulfonamide (identified as CL 75)

The title compound was synthesized following the procedure described for Example 9. The product was obtained as a yellow solid (95%).
Analytical Data:
$^1$H NMR (300 MHz; DMSO-$d_6$) δ 8.44 (br s, 1H), 8.18-8.00 (m, 4H), 7.55 (m, 2H), 7.35 (t, J=7.7 Hz, 1H), 6.65 (br s, 1H), 3.80 (m, 4H), 3.60 (m, 4H). MS: M+1 453

Example 44

Synthesis of 4-(4-(2-morpholino-4-oxo-1,4-dihydroquinolin-8-yl)-1H-1,2,3-triazol-1-yl)-N-(phenylsulfonyl)benzamide (identified as CL 78)

The title compound was synthesized following the procedure described for Example 9. The product was obtained as a yellow solid (65%).
Analytical Data:
$^1$H NMR (300 MHz; DMSO-$d_6$) δ 9.41 (br s, 1H), 8.44 (br s, 1H), 8.14 (d, J=8.5 Hz, 2H), 7.98 (m, 5H), 7.58 (m, 3H), 7.37 (br s, 1H), 6.53 (br s, 1H), 3.80 (m, 4H), 3.60 (m, 4H). MS: M+1 557

Example 45

Synthesis of N-benzyl-3-((4-(2-morpholino-4-oxo-1,4-dihydroquinolin-8-yl)-1H-1,2,3-triazol-1-yl)methyl) benzamide (identified as CL 129A)

The title compound was synthesized following the procedure described for Example 9. The product was obtained as a yellow solid (24%).
Analytical Data:
$^1$H NMR (300 MHz; DMSO-$d_6$) δ 9.13 (br t, 1H), 8.70 (br s, 1H), 8.36 (br s, 1H), 7.98-7.91 (m, 3H), 7.58-7.48 (m, 2H), 7.31-7.23 (m, 6H), 6.52 (br s, 1H), 5.78 (s, 2H), 4.47 (d, J=7.7 Hz, 2H), 3.67 (m, 4H), 3.35 (m, 4H). MS: M+1 521

Example 46

Synthesis of benzyl 3-((4-(2-morpholino-4-oxo-1,4-dihydroquinolin-8-yl)-1H-1,2,3-triazol-1-yl)methyl) benzoate (identified as FM 140)

The title compound was synthesized following the procedure described for Example 9. The product was obtained as a white solid (76%).
Analytical Data:
$^1$H NMR (300 MHz; DMSO-$d_6$) δ 8.73 (s, 1H), 8.36 (d, J=6.3 Hz, 1H), 8.04-7.93 (m, 3H), 7.71 (d, J=7.7 Hz, 1H), 7.59 (t, J=7.7 Hz, 1H), 7.44 (m, 2H), 7.36-7.26 (m, 4H), 6.48 (br s, 1H), 5.84 (s, 2H), 5.35 (s, 2H), 3.67 (m, 4H), 3.40 (m, 4H). MS: M+1 522

Example 47

Synthesis of isopropyl 3-((4-(2-morpholino-4-oxo-1,4-dihydroquinolin-8-yl)-1H-1,2,3-triazol-1-yl)methyl) benzoate (identified as FM 137)

The title compound was synthesized following the procedure described for Example 9. The product was obtained as a yellow solid (52%).
Analytical Data:
$^1$H NMR (300 MHz; DMSO-$d_6$) δ 8.70 (s, 1H), 8.35 (d, J=6.9 Hz, 1H), 8.01 (s, 1H), 7.93 (m, 2H), 7.68 (d, J=8.0 Hz, 1H), 7.57 (t, J=8.0 Hz, 1H), 7.28 (t, J=8.0 Hz, 1H), 6.46 (br s, 1H), 5.81 (s, 2H), 5.13 (kept, J 6.3 Hz, 1H), 3.65 (m, 4H), 3.40 (m, 4H), 1.31 (d, J=6.3 Hz, 6H). MS: M+1 474

Example 48

Synthesis of ethyl 3-((4-(2-morpholino-4-oxo-1,4-dihydroquinolin-8-yl)-1H-1,2,3-triazol-1-yl)methyl) benzoate (identified as FM 138)

The title compound was synthesized following the procedure described for Example 9. The product was obtained as a white solid (64%).
Analytical Data:
$^1$H NMR (300 MHz; DMSO-$d_6$) δ 8.72 (s, 1H), 8.35 (s, 1H), 8.03 (s, 1H), 7.93 (m, 2H), 7.69 (d, J=7.7 Hz, 1H), 7.58 (t, J=7.7 Hz, 1H), 7.28 (t, J=7.7 Hz, 1H), 6.45 (br s, 1H), 5.82

(s, 2H), 4.33 (quart, J=7.1 Hz, 2H), 3.67 (m, 4H), 3.38 (m, 4H), 1.30 (t, J=7.1 Hz, 3H). MS: M+1 460

Example 49

Synthesis of pyridin-4-ylmethyl 3-((4-(2-morpholino-4-oxo-1,4-dihydroquinolin-8-yl)-1H-1,2,3-triazol-1-yl)methyl)benzoate (identified as FF 19)

The title compound was synthesized following the procedure described for Example 9. The product was obtained as a yellow solid (79%).
Analytical Data:
$^1$H NMR (300 MHz; CD$_3$OD) δ 8.51 (s, 1H), 8.08 (s, 1H), 8.03 (d, J=7.7 Hz, 1H), 7.93 (d, J=7.7 Hz, 1H), 7.66 (m, 2H), 7.52 (m, 2H), 7.28 (m, 4H), 7.10 (t, J=7.7 Hz, 1H), 5.71 (s, 2H), 5.32 (s, 2H), 3.79 (m, 4H), 3.39 (m, 4H). MS: M+1 523

Example 50

Synthesis of pyridin-4-ylmethyl 3-((4-(2-morpholino-4-oxo-1,4-dihydroquinolin-8-yl)-1H-1,2,3-triazol-1-yl)methyl)benzoate (identified as FM 151)

The title compound was synthesized following the procedure described for Example 9. The product was obtained as a yellow solid (15%).
Analytical Data:
$^1$H NMR (300 MHz; CD$_3$OD) δ 8.77 (s, 1H), 8.59 (br s, 1H), 8.12 (d, J=8.5 Hz, 1H), 8.02 (d, J=6.7 Hz, 1H), 7.80 (m, 3H), 7.34 (t, J=7.1 Hz, 2H), 5.88 (s, 2H), 3.89 (m, 4H), 3.60 (m, 4H). MS: M+1 434

Example 51

Synthesis of methyl 2-((4-(2-morpholino-4-oxo-1,4-dihydroquinolin-8-yl)-1H-1,2,3-triazol-1-yl)methyl)isonicotinate (identified as FM 149)

The title compound was synthesized following the procedure described for Example 9. The product was obtained as a white solid (16%).
Analytical Data:
$^1$H NMR (300 MHz; DMSO-d$_6$) δ 8.83 (s, 1H), 8.80 (br s, 1H), 8.38 (d, J=6.9 Hz, 1H), 7.92-7.80 (m, 3H), 7.29 (m, 2H), 6.49 (br s, 1H), 5.96 (s, 2H), 3.89 (s, 3H), 3.70 (m, 4H), 3.39 (m, 4H). MS: M+1 447

Example 59

Synthesis of ethyl 3-((4-(4-methoxy-2-morpholinoquinolin-8-yl)-1H-1,2,3-triazol-1-yl)methyl) benzoate (identified as FM 125)

The title compound was synthesized following the procedure described for Example 9. The product was obtained as a yellow solid (25%).
Analytical Data:
$^1$H NMR (300 MHz; DMSO-d$_6$) δ 8.73 (s, 1H), 8.37 (d, J=6.3 Hz, 1H), 8.04 (s, 1H), 7.96 (d, J=7.7 Hz, 1H), 7.90 (d, J=7.1 Hz, 1H), 7.70 (d, J=7.7 Hz, 1H), 7.59 (t, J=7.7 Hz, 1H), 7.31 (t, J=7.7 Hz, 1H), 6.66 (s, 1H), 5.82 (s, 2H), 4.33 (quart, J=7.0 Hz, 2H), 4.01 (s, 3H), 3.70 (m, 4H), 3.53 (m, 4H), 1.31 (t, J=7.0 Hz, 3H). MS: M+1 474

Activity Evaluation of Compounds of Formula (I) on PI3Ks

Determination of the activity of some compounds of formula (I) on PI3Ks was performed by a number of direct and indirect detection methods.

In addition, cell-based assays were used to evaluate possible cytotoxic effects of the compounds of formula (I) on cell viability and proliferation.

Detection Methods of Inhibitory Effect of Formula (I) Compounds on PI3Ks

Two different detection methods—a) and b)—were used in order to evaluate the inhibitory property of formula (I) compounds on the PI3k signaling pathway.

a) Some compounds of formula (I) described herein were assayed in vitro for their ability to inhibit the lipid kinase activity of PI3Ks, by using a non-radioactive method.

In details, His and GST-tagged recombinant proteins (purchased from JenaBioscience—Germany; PI3Kα #PR-335, PI3Kβ #PR-344, PI3Kγ #PR-343, PI3Kδ #PR-345) for each isoform PI3Kα, β, γ and δ, were incubated with 10 μM of ATP, with lipid micells containg the appropriate substrate phosphatidylinositol and the phosphatidilserine, and different concentrations of the formula (I) compounds.

After 30 minutes of incubation at room temperature, the amount of ADP produced from ATP following the activation of kinase was measured with a luminescent kinase assay, ADP-Glo™ Kinase Assay (purchased from Promega—USA #V9101).

The luminescent signal positively correlates with the formed ADP and, therefore, with the kinase activity.

Samples that did not contain a PI3K inhibitory compound of formula (I)—the control samples—were assigned a relative PI3K activity value of 100.

Inhibition of PI3K lipid kinase activity is achieved when the amount of ADP—that is correlated with the PI3K activity—in the presence of the assayed compound of formula (I) is lower than the amount detected in the control samples.

For each assayed formula (I) compound, a specific IC$_{50}$ for each class I PI3K isoform was measured.

The IC$_{50}$ of a formula (I) compound is the concentration of the compound able to inhibit by 50% the kinase activity of each PI3K isoform.

The IC$_{50}$ was determined by constructing a dose-response curve and examining the inhibitory effect of different concentrations of the assayed formula (I) compounds on the ADP production.

b) Determination of the potential of compounds of formula (I) to inhibit the PI3K signaling pathway in vitro was also examined by an indirect detection method that measures the amount of phosphorylated Akt produced in cell after incubation with insulin.

Indeed, insulin is a growth factor able to activate, through its tyrosine kinase receptor, class Ia PI3Ks that in turn induce Akt phosphorylation to the formation of active phospho-Akt (P-Akt).

NIH-3T3 cells (with code #CRL-1658, purchased from American Type Culture Collection (ATCC)— USA) were seeded in a 96 well plate in presence of DMEM supplemented with 10% FBS.

Cells were incubated at 37° C. and 5% CO$_2$ for 24 h. Cells were then starved in free DMEM for 6-12 hours and stimulated with 1 μM insulin for 5 minutes in presence or in absence of compounds of formula (I) at different doses.

Stimulation was blocked by discarding the medium and adding Laemmli buffer (2% SDS, 10% glycerol, 5% 2-mercaptoethanol, 0.01% bromophenol blue and 60 mM Tris-HCl pH 6.8) to extract proteins.

Protein extracts were boiled at 95° C. for 5 minutes, loaded on a SDS-PAGE gel and transferred on a PVDF membrane.

Active phosphorylated Akt (P-Akt) was detected after overnight incubation with an anti-pAkt antibody (Cell Signaling Technology—USA, #4060) and with an anti-rabbit secondary HRP-conjugated antibody.

The signal was detected through a chemiluminescent detection system (Immobilon Western Chemiluminescent HRP Substrate #WBKLS0050, Millipore—USA).

The luminescent signal positively correlates with the formed P-Akt and, therefore, with the kinase activity. P-Akt densitometry results were normalized to α-actin.

Cells that did not contain a PI3K inhibitory compound of formula (I)—control samples—were assigned a relative PI3K activity value of 100.

For each assayed formula (I) compound, a specific $EC_{50}$ value was measured.

The $EC_{50}$ of a graded dose-response curve represents the concentration of the compound of formula (I) where 50% of its inhibitory effect on the P-Akt production is observed.

Analysis of the Effects on Cell Viability of Formula (I) Compounds

Cell-based assays were used to assess the possible cytotoxic effects of some compounds of formula (I).

To measure cytotoxic effects, a MTT cell proliferation assay was used (Roche Applied Science #11465007001). The assay is based on the cleavage of the yellow tetrazolium salt MTT to purple formazan crystals by metabolic active cells. Since reduction of MTT can only occur in metabolically active cells the level of activity is a measure of the viability of the cells and conversely the cytotoxic effects of various treatments.

Cells (NIH3T3 with code #CRL-1658, BT474 with code #HTB-20, PC3 with code #CRL-1435, HCT-116 with code #CCL-247 and DLD-1 with code #CCL-221, purchased from American Type Culture Collection (ATCC)— USA) were seeded at $2 \times 10^3$ per well in a 96 well plate and cultivated in the presence of DMEM 10% FBS at 37° C. and 5% $CO_2$ for 72 h in presence or absence of the compound/s of formula (I). Subsequently, cells were incubated with the yellow MTT solution for approximately 4 h.

Formed salt crystals were solubilized by adding the solubilization solution and incubating the plates overnight at 37° C. in a humidified atmosphere.

The plate was then read at 550-600 nm in an ELISA reader, with a reference wavelength of >650 nm. Each obtained value correlates with the metabolic status of cell and conversely to the cell viability.

Absorbance values obtained from cells that did not contain a PI3K inhibitory compound of formula (I)—control samples—were assigned a relative growth value of 100. Cytotoxic effects are achieved when obtained values with each inhibitor were lower than control.

For each formula (I) compound a dose response curve and an $EC_{50}$ for the effects on cell viability and proliferation were calculated. EC50 will define the compound concentration able to induce cytotoxicity.

Example a

Analysis of the Inhibitory Properties of Formula (I) Compounds on PI3K Activity (Assay on Lipid Micelles)

To evaluate the ability of each compound of formula (I) to inhibit the lipid kinase activity of each PI3K isoform, PI3Kα, β, γ and δ recombinant proteins (30 ng for each assay) were incubated for about 30 minutes with different concentrations of compounds.

Lipid micelles were formed by sonicating a mixture of 1 mg of phosphatidylinositol and 1 mg of phosphatidylserine. Lipid micelles were use as substrate for the PI3K lipid kinase activity. The reaction was started by adding 10 μM of ATP and 10 μM of micelles to each reaction.

After 30 minutes of incubation at room temperature, the reaction was stopped and the amount of ADP produced was measured by using the ADP-glo assay (see above).

Several compounds, listed below, showed an $IC_{50}$ value comprised between 10 nM and 10 μM:

8-(1-(2-hydroxyphenyl)-1H-1,2,3-triazol-4-yl)-2-morpholinoquinolin-4(1H)-one, TP714

2-morpholino-8-(1-phenyl-1H-1,2,3-triazol-4-yl)quinolin-4(1H)-one, CL1

8-(1-benzyl-1H-1,2,3-triazol-4-yl)-2-morpholinoquinolin-4(1H)-one, CL5

8-(1-(3-methoxyphenyl)-1H-1,2,3-triazol-4-yl)-2-morpholinoquinolin-4(1H)-one, CL6

2-morpholino-8-(1-(pyridin-4-yl)-1H-1,2,3-triazol-4-yl)quinolin-4(1H)-one, CL8

8-(1-(4-(benzyloxy)phenyl)-1H-1,2,3-triazol-4-yl)-2-morpholinoquinolin-4(1H)-one, CL9

2-(4-(4-(2-morpholino-4-oxo-1,4-dihydroquinolin-8-yl)-1H-1,2,3-triazol-1-yl)phenyl)acetonitrile, CL12

3-((4-(2-morpholino-4-oxo-1,4-dihydroquinolin-8-yl)-1H-1,2,3-triazol-1-yl)methyl)benzoic acid, CL27e 4-(4-(2-morpholino-4-oxo-1,4-dihydroquinolin-8-yl)-1H-1,2,3-triazol-1-yl)benzoic acid, CL29a 4-(4-(2-morpholino-4-oxo-1,4-dihydroquinolin-8-yl)-1H-1,2,3-triazol-1-yl)butanoic acid, CL55a 3-(4-(2-morpholino-4-oxo-1,4-dihydroquinolin-8-yl)-1H-1,2,3-triazol-1-yl)benzoic acid, CL55b 5-(4-(2-morpholino-4-oxo-1,4-dihydroquinolin-8-yl)-1H-1,2,3-triazol-1-yl)pentanoic acid, CL 64a N-benzyl-3-((4-(2-morpholino-4-oxo-1,4-dihydroquinolin-8-yl)-1H-1,2,3-triazol-1-yl)methyl)benzamide, CL 129A Table 2 below shows a comparison among TGX155, a compound described in the disclosure WO-A-01/53266 and in Billott et al. *Cancer Res.* 2009; 69: 1027-1036, and a list of compounds derived from formula (I). The data obtained on p110α demonstrate that the insertion of a N-substituted 1,2,3-triazole at the 8 position of the compounds of formula (I) confers a higher potency on p110α. In addition, the compounds of formula (I), in contrast with compounds disclosed in WO-A-01/53266, show a broad activity against all class I PI3K isoforms (p110α, p110β, p110γ, p110δ) instead of selectivity versus a single isoform.

TABLE 2

| Compound | p110α (IC50-μM) |
|---|---|
| TGX155 | >20 |
| 8-(1-(2-hydroxyphenyl)-1H-1,2,3-triazol-4-yl)-2-morpholinoquinolin-4(1H)-one, TP714 | 0.26 |
| 2-morpholino-8-(1-phenyl-1H-1,2,3-triazol-4-yl)quinolin-4(1H)-one, CL1 | 0.73 |
| 8-(1-benzyl-1H-1,2,3-triazol-4-yl)-2-morpholinoquinolin-4(1H)-one, CL5 | 0.26 |
| 2-(4-(4-(2-morpholino-4-oxo-1,4-dihydroquinolin-8-yl)-1H-1,2,3-triazol-1-yl)phenyl)acetonitrile, CL12 | 0.10 |
| 3-((4-(2-morpholino-4-oxo-1,4-dihydroquinolin-8-yl)-1H-1,2,3-triazol-1-yl)methyl)benzoic acid, CL27e | 0.02 |

TABLE 2-continued

| Compound | p110α (IC50-μM) |
|---|---|
| 4-(4-(2-morpholino-4-oxo-1,4-dihydroquinolin-8-yl)-1H-1,2,3-triazol-1-yl)benzoic acid, CL29a | 0.32 |
| 4-(4-(2-morpholino-4-oxo-1,4-dihydroquinolin-8-yl)-1H-1,2,3-triazol-1-yl)butanoic acid, CL55a | 0.100 |
| 3-(4-(2-morpholino-4-oxo-1,4-dihydroquinolin-8-yl)-1H-1,2,3-triazol-1-yl)benzoic acid, CL55b | 0.100 |
| 5-(4-(2-morpholino-4-oxo-1,4-dihydroquinolin-8-yl)-1H-1,2,3-triazol-1-yl)pentanoic acid, CL64a | 0.10 |
| N-benzyl-3-((4-(2-morpholino-4-oxo-1,4-dihydroquinolin-8-yl)-1H-1,2,3-triazol-1-yl)methyl)benzamide, CL129a | 0.14 |

Example b

Analysis of the Inhibitory Properties of Formula (I) Compounds on PI3K Activity (Cell-Based Assay)

Selected exemplary compounds of formula (I) were assayed for their ability to inhibit Akt activation following stimulation with insulin.

As described above, cells were incubated with the compounds of formula (I) listed below at different doses and subsequently stimulated with 1 μM of insulin.

The amount of P-Akt produced was measured by western blotting analysis and an $EC_{50}$ value was calculated.

Exemplary compounds herein listed showed $EC_{50}$ values from 100 nM to 10 μM:

8-(1-(2-hydroxyphenyl)-1H-1,2,3-triazol-4-yl)-2-morpholinoquinolin-4(1H)-one, TP714
2-morpholino-8-(1-phenyl-1H-1,2,3-triazol-4-yl)quinolin-4(1H)-one, CL1
8-(1-benzyl-1H-1,2,3-triazol-4-yl)-2-morpholinoquinolin-4(1H)-one, CL5
8-(1-(3-methoxyphenyl)-1H-1,2,3-triazol-4-yl)-2-morpholinoquinolin-4(1H)-one, CL6
8-(1-(4-(benzyloxy)phenyl)-1H-1,2,3-triazol-4-yl)-2-morpholinoquinolin-4(1H)-one, CL9
2-(4-(4-(2-morpholino-4-oxo-1,4-dihydroquinolin-8-yl)-1H-1,2,3-triazol-1-yl)phenyl)acetonitrile, CL12
methyl 3-((4-(2-morpholino-4-oxo-1,4-dihydroquinolin-8-yl)-1H-1,2,3-triazol-1-yl)methyl)benzoate, CL27c

Example c

Analysis of Effects on Cell Viability

The effects of the compounds of formula (I) on cell viability were measured by MTT assay on tumor cell lines (NIH3T3, BT474, PC3, HCT-116 and DLD-1).

Formula (I) compounds were added to the medium at different doses for a period of 72 h and the cell viability was measured.

The following compounds have shown cytotoxicity on cell in the range of 10-1 μM.

methyl 3-((4-(2-morpholino-4-oxo-1,4-dihydroquinolin-8-yl)-1H-1,2,3-triazol-1-yl)methyl)benzoate, CL27c
8-(1-benzyl-1H-1,2,3-triazol-4-yl)-2-morpholinoquinolin-4(1H)-one, CL5

Naturally, while the principle of the invention remains the same, the details of construction and the embodiments may widely vary with respect to what has been described and illustrated purely by way of example, without departing from the scope of the present invention.

The invention claimed is:

1. Compound of formula (I):

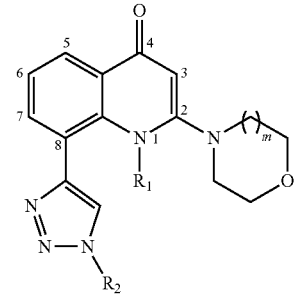

(1)

wherein $R^1$ is H, or straight or branched, substituted or unsubstituted $C_{1-8}$ alkyl, $R^2$ is H, straight or branched, substituted or unsubstituted $C_{1-8}$ alkyl, substituted or unsubstituted $C_{3-6}$ cycloalkyl, $Ar^2$, $(CH_2)_n$—$C_{1-8}$ alkyl, or $(CH_2)_n$—$Ar^2$, n being an integer 1 to 4, m is an integer 1 to 2, $Ar^2$ is a substituted or unsubstituted aryl or heteroaryl group, pharmaceutically acceptable tautomers and/or hydrates and/or solvates and/or salts and/or pro-drugs thereof.

2. Compound according to claim 1, wherein when $R^1$ is a substituted $C_{1-8}$ alkyl, the one or more substituents are independently selected from halogen atoms, —$NH_2$, —$NHR^3$, —$NR^3R^4$, —OH, —$OR^3$, —$S(O)R^3$, —$S(O)_2R^3$, —NHCOR$^3$, —$NHSO_2R^3$, —$CONHR^3$, —$CONR^3R^4$, —$SO_2NHR^3$, —COOH, —$COOR^3$, wherein $R^3$ and $R^4$ are identical or different from each other and independently selected from —H, straight or branched, substituted or unsubstituted $C_{1-8}$ alkyl, substituted or unsubstituted $C_{3-6}$ cycloalkyl, $Ar^3$ and $Ar^4$ groups, $Ar^3$ and $Ar^4$ are independently a substituted or unsubstituted aryl or heteroaryl group.

3. Compound according to claim 1, wherein when $R^2$ is selected from a substituted $C_{1-8}$ alkyl, $C_3$-$C_6$ cycloalkyl, and $(CH_2)_n$—$C_{1-8}$ alkyl, the one or more substituents are independently selected from halogen atoms, tetrazole, —COOH, —OH, —$NH_2$, —$COOR^5$, —$NO_2$, —$CF_3$, —CN, —$OR^5$, —$CONH_2$, —$CONHR^5$, —$CONR^5R^6$, —$NHR^5$, —$NR^5R^6$, —$NHCOR^5$, —$NHSO_2R^5$, —$SO_2NHR^5$, —$SO_2NR^5R^6$, —$NHCONHR^5$, —$NHCONR^5R^6$, —$NHCOR^5$, wherein $R^5$ and $R^6$ are identical or different from each other and independently selected from —H, straight or branched, substituted or unsubstituted $C_{1-8}$ alkyl, substituted or unsubstituted $C_{3-6}$ cycloalkyl, $Ar^5$ and $Ar^6$ groups, $Ar^5$ and $Ar^6$ are independently a substituted or unsubstituted aryl or heteroaryl group.

4. Compound according to claim 2, wherein when any of $R^3$, $R^4$, $R^5$, $R^6$, if present, are independently selected from a substituted $C_{1-8}$ alkyl and $C_{3-6}$ cycloalkyl, the one or more substituents are independently selected from halogen atoms, tetrazole, —COOH, —OH, —$NH_2$, —$COOR^7$, —$NO_2$, —$CF_3$, —CN, —$OR^7$, —$CONH_2$, —$CONHR^7$, —$CONR^7R^8$, —$NHR^7$, —$NR^7R^8$, —$NHCOR^7$, —$NHSO_2R^7$, —$SO_2NHR^7$, —$SO_2NR^7R^8$, —$NHCONHR^7$, —$NHCONR^7R^8$, —$NHCOR^7$, wherein
R⁷ and R⁸ are identical or different from each other and independently selected from —H, straight or branched, substituted or unsubstituted $C_{1-8}$ alkyl, substituted or unsubstituted $C_{3-6}$ cycloalkyl, $Ar^7$ and $Ar^8$ groups,
$Ar^7$ and $Ar^8$ are independently a substituted or unsubstituted aryl or heteroaryl group.

5. Compound according to claim 1, wherein when any of $Ar^2$, $Ar^3$, $Ar^4$, $Ar^5$, $Ar^6$, $Ar^7$, $Ar^8$ groups, if present, are independently selected from a substituted aryl or heteroaryl group, the one or more substituents are independently selected from halogen atoms, tetrazole, —COOH, —OH, —NH₂, —COOR⁹, —NO₂, —CF₃, —OCF₃, —CN, —OR⁹, —CONH₂, —CONHR⁹, —CONR⁹R¹⁰, —NHR⁹, —NHCOR⁹, —NHSO₂R⁹, —SO₂NHR⁹,
wherein
R⁹ and R¹⁰ are identical or different from each other and independently selected from —H, straight or branched, substituted or unsubstituted $C_{1-8}$ alkyl, substituted or unsubstituted $C_{3-6}$ cycloalkyl, $Ar^9$ and $Ar^{10}$ groups,
$Ar^9$ and $Ar^{10}$ are independently a substituted or unsubstituted aryl or heteroaryl group.

6. Compound according to claim 1, wherein any of $Ar^2$, $Ar^3$, $Ar^4$, $Ar^5$, $Ar^6$, $Ar^7$, $Ar^8$, $Ar^9$, $Ar^{10}$ groups, if present, are independently selected from benzene, furan, thiophene, pyrrolidine, pyrrole, pyrazole, imidazole, oxazole, isooxazole, thiazole, isothiazole, 1,2,3-oxadiazole, 1,2,4-oxadiazole, 1,2,5-oxadiazole, pyridine, pyrididazine, pyrimidine, pyrazine, naphthalene, indole, isoindole, indolizine, benzofuran, benzothiophene, quinoline, isoquinoline, quinoxaline, carbazole, 1,2,3-triazole, 1H-indazole, 1H-benzo[d]imidazole, benzo[d]thiazol-2-amine.

7. Compound according to claim 1, selected from:
8-(1-benzyl-1H-1,2,3-triazol-4-yl)-2-morpholinoquinolin-4(1H)-one,
2-morpholino-8-(1-phenyl-1H-1,2,3-triazol-4-yl)quinolin-4(1H)-one,
2-(4-(4-(2-morpholino-4-oxo-1,4-dihydroquinolin-8-yl)-1H-1,2,3-triazol-1-yl)phenyl)acetonitrile,
8-(1-(3-methoxyphenyl)-1H-1,2,3-triazol-4-yl)-2-morpholinoquinolin-4(1H)-one,
2-morpholino-8-(1-(pyridin-4-yl)-1H-1,2,3-triazol-4-yl)quinolin-4(1H)-one,
8-(1-(2-hydroxyphenyl)-1H-1,2,3-triazol-4-yl)-2-morpholinoquinolin-4(1H)-one,
8-(1-(4-(benzyloxy)phenyl)-1H-1,2,3-triazol-4-yl)-2-morpholinoquinolin-4(1H)-one,
Methyl 4-((4-(2-morpholino-4-oxo-1,4-dihydroquinolin-8-yl)-1H-1,2,3-triazol-1-yl)methyl)benzoate,
2-((4-(2-morpholino-4-oxo-1,4-dihydroquinolin-8-yl)-1H-1,2,3-triazol-1-yl)methyl)benzonitrile,
methyl 3-((4-(2-morpholino-4-oxo-1,4-dihydroquinolin-8-yl)-1H-1,2,3-triazol-1-yl)methyl)benzoate,
8-(1-(2-(1H-indol-3-yl)ethyl)-1H-1,2,3-triazol-4-yl)-2-morpholinoquinolin-4(1H)-one,
3-((4-(2-morpholino-4-oxo-1,4-dihydroquinolin-8-yl)-1H-1,2,3-triazol-1-yl)methyl)benzoic acid,
8-(1-(4-methoxyphenyl)-1H-1,2,3-triazol-4-yl)-2-morpholinoquinolin-4(1H)-one,
4-(4-(2-morpholino-4-oxo-1,4-dihydroquinolin-8-yl)-1H-1,2,3-triazol-1-yl)benzoic acid,
8-(1-(3-hydroxyphenyl)-1H-1,2,3-triazol-4-yl)-2-morpholinoquinolin-4(1H)-one,
8-(1-(3-hydroxy-4-methoxyphenyl)-1H-1,2,3-triazol-4-yl)-2-morpholinoquinolin-4(1H)-one,
8-(1-(4-chlorophenyl)-1H-1,2,3-triazol-4-yl)-2-morpholinoquinolin-4(1H)-one,
8-(1-(4-methoxy-3-nitrophenyl)-1H-1,2,3-triazol-4-yl)-2-morpholinoquinolin-4(1H)-one,
8-(1-(3,5-dimethoxyphenyl)-1H-1,2,3-triazol-4-yl)-2-morpholinoquinolin-4(1H)-one,
methyl 4-(4-(2-morpholino-4-oxo-1,4-dihydroquinolin-8-yl)-1H-1,2,3-triazol-1-yl)benzoate,
8-(1-(benzo[d][1,3]dioxol-5-yl)-1H-1,2,3-triazol-4-yl)-2-morpholinoquinolin-4(1H)-one,
N-(4-methoxy-3-(4-(2-morpholino-4-oxo-1,4-dihydroquinolin-8-yl)-1H-1,2,3-triazol-1-yl)phenyl)acetamide,
8-(1-(4-hydroxy-2-methylphenyl)-1H-1,2,3-triazol-4-yl)-2-morpholinoquinolin-4(1H)-one,
2-morpholino-8-(1-(quinolin-3-yl)-1H-1,2,3-triazol-4-yl)quinolin-4(1H)-one,
2-morpholino-8-(1-(4-(trifluoromethoxy)phenyl)-1H-1,2,3-triazol-4-yl)quinolin-4(1H)-one,
2-morpholino-8-(1-(naphthalen-1-yl)-1H-1,2,3-triazol-4-yl)quinolin-4(1H)-one,
2-morpholino-8-(1-(naphthalen-2-yl)-1H-1,2,3-triazol-4-yl)quinolin-4(1H)-one,
8-(1-(4-aminophenyl)-1H-1,2,3-triazol-4-yl)-2-morpholinoquinolin-4(1H)-one,
8-(1-(3-methoxy-5-(trifluoromethoxy)phenyl)-1H-1,2,3-triazol-4-yl)-2-morpholinoquinolin-4(1H)-one,
8-(1-(2-methoxyphenyl)-1H-1,2,3-triazol-4-yl)-2-morpholinoquinolin-4(1H)-one,
3-(4-(2-morpholino-4-oxo-1,4-dihydroquinolin-8-yl)-1H-1,2,3-triazol-1-yl)benzoic acid,
8-(1-(3,4-dimethoxyphenyl)-1H-1,2,3-triazol-4-yl)-2-morpholinoquinolin-4(1H)-one,
4-(4-(2-morpholino-4-oxo-1,4-dihydroquinolin-8-yl)-1H-1,2,3-triazol-1-yl)butanoic acid,
methyl 3-(4-(2-morpholino-4-oxo-1,4-dihydroquinolin-8-yl)-1H-1,2,3-triazol-1-yl)benzoate,
5-(4-(2-morpholino-4-oxo-1,4-dihydroquinolin-8-yl)-1H-1,2,3-triazol-1-yl)pentanoic acid,
6-(4-(2-morpholino-4-oxo-1,4-dihydroquinolin-8-yl)-1H-1,2,3-triazol-1-yl)hexanoic acid,
N-(3-((4-(2-morpholino-4-oxo-1,4-dihydroquinolin-8-yl)-1H-1,2,3-triazol-1-yl)methyl)phenyl) benzenesulfonamide,
4-(4-(2-morpholino-4-oxo-1,4-dihydroquinolin-8-yl)-1H-1,2,3-triazol-1-yl)benzenesulfonamide,
4-(4-(2-morpholino-4-oxo-1,4-dihydroquinolin-8-yl)-1H-1,2,3-triazol-1-yl)-N-(phenylsulfonyl)benzam ide,
8-(1-(3-(1H-tetrazol-5-yl)benzyl)-1H-1,2,3-triazol-4-yl)-2-morpholinoquinolin-4(1H)-one,
8-(1-(4-(1H-tetrazol-5-yl)phenyl)-1H-1,2,3-triazol-4-yl)-2-morpholinoquinolin-4(1H)-one,
N-benzyl-3-((4-(2-morpholino-4-oxo-1,4-dihydroquinolin-8-yl)-1H-1,2,3-triazol-1-yl)methyl)benzamide,
N,N-diethyl-3-((4-(2-morpholino-4-oxo-1,4-dihydroquinolin-8-yl)-1H-1,2,3-triazol-1-yl)methyl)benzamide,
N-cyclopropyl-3-((4-(2-morpholino-4-oxo-1,4-dihydroquinolin-8-yl)-1H-1,2,3-triazol-1-yl)methyl)benzamide,
N-methyl-4-(4-(2-morpholino-4-oxo-1,4-dihydroquinolin-8-yl)-1H-1,2,3-triazol-1-yl)-N-(phenylsulfonyl)benzamide,
benzyl 3-((4-(2-morpholino-4-oxo-1,4-dihydroquinolin-8-yl)-1H-1,2,3-triazol-1-yl)methyl)benzoate,
isopropyl 3-((4-(2-morpholino-4-oxo-1,4-dihydroquinolin-8-yl)-1H-1,2,3-triazol-1-yl)methyl)benzoate,
ethyl 3-((4-(2-morpholino-4-oxo-1,4-dihydroquinolin-8-yl)-1H-1,2,3-triazol-1-yl)methyl)benzoate, pyridin-4-ylmethyl 3-((4-(2-morpholino-4-oxo-1,4-dihydroquinolin-8-yl)-1H-1,2,3-triazol-1-yl)methyl)benzoate
methyl 2-((4-(2-morpholino-4-oxo-1,4-dihydroquinolin-8-yl)-1H-1,2,3-triazol-1-yl)methyl)isonicotinate,
2-((4-(2-morpholino-4-oxo-1,4-dihydroquinolin-8-yl)-1H-1,2,3-triazol-1-yl)methyl)isonicotinic acid,
methyl 3-((4-(1-methyl-2-morpholino-4-oxo-1,4-dihydroquinolin-8-yl)-1H-1,2,3-triazol-1-yl)methyl)benzoate,
8-(1-(2-hydroxyphenyl)-1H-1,2,3-triazol-4-yl)-1-methyl-2-morpholinoquinolin-4(1H)-one,
3-((4-(1-methyl-2-morpholino-4-oxo-1,4-dihydroquinolin-8-yl)-1H-1,2,3-triazol-1-yl)methyl)benzoic acid,
benzyl 3-((4-(1-methyl-2-morpholino-4-oxo-1,4-dihydroquinolin-8-yl)-1H-1,2,3-triazol-1-yl)methyl)benzoate,
ethyl 3-((4-(1-methyl-2-morpholino-4-oxo-1,4-dihydroquinolin-8-yl)-1H-1,2,3-triazol-1-yl)methyl)benzoate,
butyl 3-((4-(2-morpholino-4-oxo-1,4-dihydroquinolin-8-yl)-1H-1,2,3-triazol-1-yl)methyl)benzoate,
2-morpholinoethyl 3-((4-(2-morpholino-4-oxo-1,4-dihydroquinolin-8-yl)-1H-1,2,3-triazol-1-yl)methyl)benzoate,
isopentyl 3-((4-(2-morpholino-4-oxo-1,4-dihydroquinolin-8-yl)-1H-1,2,3-triazol-1-yl)methyl)benzoate,
pivaloyloxymethyl 3-((4-(2-morpholino-4-oxo-1,4-dihydroquinolin-8-yl)-1H-1,2,3-triazol-1-yl)methyl)benzoate,
1-(pivaloyloxy)ethyl 3-((4-(2-morpholino-4-oxo-1,4-dihydroquinolin-8-yl)-1H-1,2,3-triazol-1-yl)methyl)benzoate,
1-(tert-butoxycarbonyloxy)ethyl 3-((4-(2-morpholino-4-oxo-1,4-dihydroquinolin-8-yl)-1H-1,2,3-triazol-1-yl)methyl)benzoate,
1-(cyclohexyloxycarbony)oxy)ethyl 3-((4-(2-morpholino-4-oxo-1,4-dihydroquinolin-8-yl)-1H-1,2,3-triazol-1-yl)methyl)benzoate,
2-morpholino-8-(1 4(1-oxo-1,3-dihydroisobenzofuran-4-yl)methyl)-1H-1,2,3-triazol-4-yl)quinolin-4(1H)-one,
2-morpholino-8-(1 4(1-oxoisochroman-5-yl)methyl)-1H-1,2,3-triazol-4-yl)quinolin-4(1H)-one,
heptyl 3-((4-(2-morpholino-4-oxo-1,4-dihydroquinolin-8-yl)-1H-1,2,3-triazol-1-yl)methyl)benzoate,
undecyl 3-((4-(2-morpholino-4-oxo-1,4-dihydroquinolin-8-yl)-1H-1,2,3-triazol-1-yl)methyl)benzoate,
octadecyl 3-((4-(2-morpholino-4-oxo-1,4-dihydroquinolin-8-yl)-1H-1,2,3-triazol-1-yl)methyl)benzoate,
8-(1-benzyl-1H-1,2,3-triazol-4-yl)-2-(1,4-oxazepan-4-yl)quinolin-4(1H)-one,
2-(1,4-oxazepan-4-yl)-8-(1-phenyl-1H-1,2,3-triazol-4-yl)quinolin-4(1H)-one,
2-(4-(4-(2-(1,4-oxazepan-4-yl)-4-oxo-1,4-dihydroquinolin-8-yl)-1H-1,2,3-triazol-1-yl)phenyl)acetonitrile,
8-(1-(3-methoxyphenyl)-1H-1,2,3-triazol-4-yl)-2-(1,4-oxazepan-4-yl)quinolin-4(1H)-one,
2-(1,4-oxazepan-4-yl)-8-(1-(pyridin-4-yl)-1H-1,2,3-triazol-4-yl)quinolin-4(1H)-one,
8-(1-(2-hydroxyphenyl)-1H-1,2,3-triazol-4-yl)-2-(1,4-oxazepan-4-yl)quinolin-4(1H)-one,
8-(1-(4-(benzyloxy)phenyl)-1H-1,2,3-triazol-4-yl)-2-(1,4-oxazepan-4-yl)quinolin-4(1H)-one,
methyl 4-((4-(2-(1,4-oxazepan-4-yl)-4-oxo-1,4-dihydroquinolin-8-yl)-1H-1,2,3-triazol-1-yl)methyl)benzoate,
2-((4-(2-(1,4-oxazepan-4-yl)-4-oxo-1,4-dihydroquinolin-8-yl)-1H-1,2,3-triazol-1-yl)methyl)benzonitrile,
methyl 3-((4-(2-(1,4-oxazepan-4-yl)-4-oxo-1,4-dihydroquinolin-8-yl)-1H-1,2,3-triazol-1-yl)methyl)benzoate,
8-(1-(2-(1H-indol-3-yl)ethyl)-1H-1,2,3-triazol-4-yl)-2-(1,4-oxazepan-4-yl)quinolin-4(1H)-one,
3-((4-(2-(1,4-oxazepan-4-yl)-4-oxo-1,4-dihydroquinolin-8-yl)-1H-1,2,3-triazol-1-yl)methyl)benzoic acid,
8-(1-(4-methoxyphenyl)-1H-1,2,3-triazol-4-yl)-2-(1,4-oxazepan-4-yl)quinolin-4(1H)-one,
4-(4-(2-(1,4-oxazepan-4-yl)-4-oxo-1,4-dihydroquinolin-8-yl)-1H-1,2,3-triazol-1-yl)benzoic acid,
8-(1-(3-hydroxyphenyl)-1H-1,2,3-triazol-4-yl)-2-(1,4-oxazepan-4-yl)quinolin-4(1H)-one,
8-(1-(3-hydroxy-4-methoxyphenyl)-1H-1,2,3-triazol-4-yl)-2-(1,4-oxazepan-4-yl)quinolin-4(1H)-one,
8-(1-(4-chlorophenyl)-1H-1,2,3-triazol-4-yl)-2-(1,4-oxazepan-4-yl)quinolin-4(1H)-one,
8-(1-(4-methoxy-3-nitrophenyl)-1H-1,2,3-triazol-4-yl)-2-(1,4-oxazepan-4-yl)quinolin-4(1H)-one,
8-(1-(3,5-dimethoxyphenyl)-1H-1,2,3-triazol-4-yl)-2-(1,4-oxazepan-4-yl)quinolin-4(1H)-one,
methyl 4-(4-(2-(1,4-oxazepan-4-yl)-4-oxo-1,4-dihydroquinolin-8-yl)-1H-1,2,3-triazol-1-yl)benzoate,
8-(1-(benzo[d][1,3]dioxol-5-yl)-1H-1,2,3-triazol-4-yl)-2-(1,4-oxazepan-4-yl)quinolin-4(1H)-one,
N-(3-(4-(2-(1,4-oxazepan-4-yl)-4-oxo-1,4-dihydroquinolin-8-yl)-1H-1,2,3-triazol-1-yl)-4-methoxyphenyl)acetamide,
8-(1-(4-hydroxy-2-methylphenyl)-1H-1,2,3-triazol-4-yl)-2-(1,4-oxazepan-4-yl)quinolin-4(1H)-one,
2-(1,4-oxazepan-4-yl)-8-(1-(quinolin-3-yl)-1H-1,2,3-triazol-4-yl)quinolin-4(1H)-one,
2-(1,4-oxazepan-4-yl)-8-(1-(4-(trifluoromethoxy)phenyl)-1H-1,2,3-triazol-4-yl)quinolin-4(1H)-one,
8-(1-(naphthalen-1-yl)-1H-1,2,3-triazol-4-yl)-2-(1,4-oxazepan-4-yl)quinolin-4(1H)-one,
8-(1-(naphthalen-2-yl)-1H-1,2,3-triazol-4-yl)-2-(1,4-oxazepan-4-yl)quinolin-4(1H)-one,
8-(1-(4-aminophenyl)-1H-1,2,3-triazol-4-yl)-2-(1,4-oxazepan-4-yl)quinolin-4(1H)-one,
8-(1-(3-methoxy-5-(trifluoromethoxy)phenyl)-1H-1,2,3-triazol-4-yl)-2-(1,4-oxazepan-4-yl)quinolin-4(1H)-one,
8-(1-(2-methoxyphenyl)-1H-1,2,3-triazol-4-yl)-2-(1,4-oxazepan-4-yl)quinolin-4(1H)-one,
3-(4-(2-(1,4-oxazepan-4-yl)-4-oxo-1,4-dihydroquinolin-8-yl)-1H-1,2,3-triazol-1-yl)benzoic acid,
8-(1-(3,4-dimethoxyphenyl)-1H-1,2,3-triazol-4-yl)-2-(1,4-oxazepan-4-yl)quinolin-4(1H)-one,
4-(4-(2-(1,4-oxazepan-4-yl)-4-oxo-1,4-dihydroquinolin-8-yl)-1H-1,2,3-triazol-1-yl)butanoic acid,
methyl 3-(4-(2-(1,4-oxazepan-4-yl)-4-oxo-1,4-dihydroquinolin-8-yl)-1H-1,2,3-triazol-1-yl)benzoate,
5-(4-(2-(1,4-oxazepan-4-yl)-4-oxo-1,4-dihydroquinolin-8-yl)-1H-1,2,3-triazol-1-yl)pentanoic acid,
6-(4-(2-(1,4-oxazepan-4-yl)-4-oxo-1,4-dihydroquinolin-8-yl)-1H-1,2,3-triazol-1-yl)hexanoic acid,
N-(3-((4-(2-(1,4-oxazepan-4-yl)-4-oxo-1,4-dihydroquinolin-8-yl)-1H-1,2,3-triazol-1-yl)methyl)phenyl)benzenesulfonamide,
4-(4-(2-(1,4-oxazepan-4-yl)-4-oxo-1,4-dihydroquinolin-8-yl)-1H-1,2,3-triazol-1-yl)benzenesulfonamide,
4-(4-(2-(1,4-oxazepan-4-yl)-4-oxo-1,4-dihydroquinolin-8-yl)-1H-1,2,3-triazol-1-yl)-N-(phenylsulfonyl)benzamide,
8-(1-(3-(1H-tetrazol-5-yl)benzyl)-1H-1,2,3-triazol-4-yl)-2-(1,4-oxazepan-4-yl)quinolin-4(1H)-one,
8-(1-(4-(1H-tetrazol-5-yl)phenyl)-1H-1,2,3-triazol-4-yl)-2-(1,4-oxazepan-4-yl)quinolin-4(1H)-one.

8. Pharmaceutical composition comprising at least one compound according to claim 1 and a pharmaceutically acceptable carrier and/or vehicle.

* * * * *